United States Patent [19]
Seizinger et al.

[11] Patent Number: 5,872,214
[45] Date of Patent: Feb. 16, 1999

[54] NF2 ISOFORMS

[75] Inventors: Bernd R. Seizinger, Stockton; Nikolai A. Kley; Albert B. Bianchi, both of Princeton, all of N.J.

[73] Assignee: Bristol-Myers Squibb Company, New York, N.Y.

[21] Appl. No.: 628,145

[22] Filed: Apr. 4, 1996

Related U.S. Application Data

[62] Division of Ser. No. 179,738, Jan. 10, 1994, Pat. No. 5,578,462.

[51] Int. Cl.⁶ ...................................................... C07K 1/00
[52] U.S. Cl. ................................................................ 530/350
[58] Field of Search .............................................. 530/350

[56] References Cited

U.S. PATENT DOCUMENTS

| | | | |
|---|---|---|---|
| 5,578,462 | 11/1996 | Seizinger et al. | 435/69.1 |
| 5,707,863 | 1/1998 | Trofatter et al. | 435/320.1 |

OTHER PUBLICATIONS

Ngo et al. (1994) Computational Complexity, Protein Structure Prediction, and the Levinthal Paradox. In: The Protein Folding Problem and Tertiary Structure Prediction, Eds. Merz et al., Birkhauser, Boston, MA, pp. 491–495, Jan. 1994.

Claudio et al., "Cloning of Mouse Schwannomin: A Homologue of A Human Tumor Suppressor Gene", (1993) *Molecular Biol. of the Cell, 33rd Annual Mtg. of the American Society for Cell Biol.* Dec. 11–19, 1993, 355a:2058.

Discher et al., Mechanochemistry of the alternatively spliced spectrin–actin binding domain in membrane skeletal protein 4.1 (1993) *J. Biol. Chem.* 268:7186–7195.

Fontaine et al., Parental origin of chromosome 22 loss in sporadic and NF2 neuromas, (1991) *Genomics* 10:280–283.

Luna et al., Cytoskeleton–plasma membrane interactions, (1992) *Science* 258:955–964.

Rouleau et al., Genetic linkage of bilateral acoustic neurofibromatosis to a DNA marker on chromosome 22, (1987) *Nature* 329:246–248.

Rouleau et al., Flanking markers bracket the neurofibromatosis type 2 (NF2) gene on chromosome 22, (1990) *Am. J. Hum. Genet.* 46:323–328.

Rouleau et al., Alteration in a new gene encoding a putative membrane–organizing protein causes neuro–fibromatosis type 2, (1993) *Nature* 363:515–521.

Seizinger et al., Loss of genes on chromosome 22 in tumorigenesis of human acoustic neuroma, (1986) *Nature* 322:644–647.

Seizinger et al., Common pathogenetic mechanism for three tumor types in bilateral acoustic neurofibromatosis, (1987) *Science* 236:317–319.

Seizinger et al., Molecular genetic appraoch to human meningioma: Loss of genes on chromosome 22, (1987) *Proc. Natl. Acad. Sci. USA* 84:5419–5423.

Seizinger et al., Report of the committee on chromosome and gene loss in human neoplasia, (1991) *Cytogenet. Cell Genet.* 58:1080–1096.

Trofatter et al., A novel moesin–, ezrin–, radixin–like gene is a candidate for the neurofibromatosis 2 tumor suppressor, (1993) *Cell* 72:791–800.

Wertelecki et al., Neurofibromatosis 2: Clinical and DNA linkage studies of a large kindred, (1988) *N. Engl. J. Med.* 319:278–283.

Wolff et al., Analysis of chromosome 22 deletions in neurofibromatosis type 2–related tumors, (1992) *Am. J. Hum. Genet.* 51:478–485.

*Primary Examiner*—Robert A. Wax
*Assistant Examiner*—Einar Stole
*Attorney, Agent, or Firm*—Robins & Associates

[57] ABSTRACT

Novel human and mouse NF2 transcript isoforms and proteins encoded thereby, are disclosed. The isoforms are found in a variety of tissue and tumor types and represent differential processing of genomic DNA sequences, at the level of transcription, resulting in variant proteins. The isoforms provide useful tools for the analysis of the normal function of tumor suppressor factors, such as the merlin protein, and also provide useful markers for the detection of NF2 disease.

4 Claims, 17 Drawing Sheets

FIG. 1A

```
                                                 5'-gc gcc cgg tac ctc gcg
                                                    Ala Arg Lys Gln Pro Lys  20
Mouse                                               Ala Arg Lys Gln Pro Lys
Mouse
Human 1 ATG GCC GGA GCC ATC GCT TCT CGC ATG AGC TCA CTC AAG CTC GCG
Mouse   Met Ala Gly Ala Ile Ala Ser Arg Met Ser Phr Ser Leu Lys Pro Lys
Mouse
Human 61 ACA TTC ACG GTG CGG ATC GTC ACC ATG GAG TTC AAC TGC GAG ATG AAA
Mouse   Thr Phe Thr Val Arg Ile Val Thr Met Glu Phe Asn Cys Glu Met Lys  40
Mouse
Human 121 TGG AAG GGG AAG GAC CTG TTT GAT TTG GTG TGC CGG ACA CTG GGG GAA ACC TGG
Mouse   Trp Lys Gly Lys Asp Leu Phe Asp Leu Val Cys Arg Thr Leu Gly Glu Thr Trp  60
Mouse
Human 181 TTC TTT GGA CTG CAG TAT ACA ATC AAG ATG GAC ACG GTG GCC CTC AAA ATG GAC AAG AAG
Mouse   Phe Phe Gly Leu Gln Tyr Thr Ile Lys Met Asp Thr Val Ala Leu Lys Met Asp Lys Lys  80
Mouse
Human 241 GTG TTG GAT CAT GAT GTT TCG AAG GAA GAG CCA GTT CAA GAG ATC ACG TTT CAC TTT GCC AAA TTT
Mouse   Val Leu Asp His Asp Val Ser Lys Glu Glu Pro Val Gln Glu Ile Thr Phe His Phe Ala Lys Phe  100
Mouse
Human 301 TAT CCT GAA AAT GCT GCT GAG GAG GAG GTA CTA GTT CAA GAG GTC TAC TGC CCT GAG GCG TCC GTG CTC TTA
Mouse   Tyr Pro Glu Asn Ala Ala Glu Glu Glu Leu Leu Val Gln Glu Val Tyr Cys Pro Pro Glu Ala Ser Val Leu  120
Mouse
Human 361 CAG GTG AAG CAG ATT TTG CTG GAT GAA AAG GTC TAC TGC CCT GAG GCG TCC GTG CTC
Mouse   Gln Val Lys Gln Ile Leu Leu Asp Glu Lys Val Tyr Cys Pro Glu Ala Ser Val Leu  140
        Ile
Mouse
Human 421 TTG GCG TCA TAT GCT GTC CAG AAG GCC TAT GAC TAT GGC GAC TAT GAC CCC TCT GTG CAC AAG CGG
Mouse   Leu Ala Ser Tyr Ala Val Gln Lys Ala Tyr Asp Tyr Gly Asp Tyr Asp Pro Ser Val His Lys Arg  160
Mouse
Human 481 GGA TTT TTA GCC CAA GAG GAA TTG CTC CCG AAA CTC TAT ATA CTC AAT CTC TAT CAG ACT
Mouse   Gly Phe Leu Ala Gln Glu Glu Leu Leu Pro Lys Leu Tyr Ile Leu Asn Leu Tyr Gln Met Thr  180
Mouse
Human 541 CCG GAA ATG TGG GAG GAG AGA ATT ACG GCT TGG TAT TAT GCC GAG CAC CGG GGC AGA GCC AGG
Mouse   Pro Glu Met Trp Glu Glu Arg Ile Thr Ala Trp Tyr Tyr Ala Glu His Arg Gly Arg Ala Arg  200
Mouse
Human
```

FIG. 1B

```
Mouse   601  GAT GAA GCT GAA ATG GAG TAT TTG AAG ATA GCT CAG GAC CTG GAG ATG TAT GGT GTG AAC
             Asp Glu Ala Glu Met Glu Tyr Leu Lys Ile Ala Gln Asp Leu Glu Met Tyr Gly Val Asn 220
Mouse
Human Mouse   661  TAC TTT ACA ATC CGG AAT AAA AAG GGC ACA GAG TTG CTT CTT GGA GTG GAT GCT CTT GGG
             Tyr Phe Thr Ile Arg Asn Lys Lys Gly Thr Glu Leu Leu Leu Gly Val Asp Ala Leu Gly 240
Mouse        Ala
Human Mouse   721  CTT CAT ATC TAT GAC CCT GAG AAC AGG CTG ACC CCC AAG ATC TCC TTC CCA TGG AAT GAA
             Leu His Ile Tyr Asp Pro Glu Asn Arg Leu Thr Pro Lys Ile Ser Phe Pro Trp Asn Glu 260
Mouse
Human Mouse   781  ATC CGA AAC ATC TCC TAC AGC GAC AAG TTT ACT ATT AAA CCA GAT AAG AAA ATT
             Ile Arg Asn Ile Ser Tyr Ser Asp Lys Phe Thr Ile Lys Pro Asp Lys Lys Ile 280
Mouse
Human Mouse   841  GAT GTC TTC AAA TTT AAC TCC TCA AAG CTT CGT GTT CTT CAG ATT CTG CAG CTA TGT
             Asp Val Phe Lys Phe Asn Ser Ser Lys Leu Arg Val Asn Lys Leu Gln Ile Leu Gln Leu Cys 300
Mouse
Human Mouse   901  ATT GGG AAC CAT GAG CTA TTT ATG CGA GCC AGG GAA GAG CAG ATG CAG AGG CAG CGG CAG
             Ile Gly Asn His Asp Leu Phe Met Arg Ala Arg Glu Glu Gln Met Glu Arg Gln Val Gln Gln 320
Mouse
Human Mouse   961  ATG AAA GCC CAG AAG CAG ATG GAA GAA GCA ACG AAG GCT AGA AGA GAT GAG TTA GAG AGG
             Met Lys Ala Gln Lys Gln Met Glu Glu Ala Thr Lys Ala Arg Arg Asp Arg Glu Arg Leu Ala 340
Mouse
Human Mouse  1021  CGA GAG AAG CAG ATG GAG GAG CGG CGG AAG ATG GCC GAG AAT GAA GCT CTG GCT AGG AGG CTC
             Arg Glu Lys Gln Met Glu Glu Arg Arg Lys Met Ala Glu Asn Glu Ala Leu Arg Arg Leu 360
Mouse
Human Mouse  1081  CTG CAG ATG AAA GAA GAA GCA ACG ATG GCC AAT GAA GCT CTG TCT GAG ACA
             Leu Gln Met Lys Glu Glu Ala Thr Met Ala Asn Glu Ala Leu Met Arg Ser Glu Glu Thr 380
Mouse
Human Mouse  1141  GCT GAT CTG TTG GCT GAA AAG GCT CAG ATC ACA GAG GAG GAG GCC AAG CTT TTG GCA CAA
             Ala Asp Leu Leu Ala Glu Lys Ala Gln Ile Thr Glu Glu Glu Ala Lys Leu Leu Ala Gln 400
Mouse
Human
```

```
Mouse  1201 AAG GCT GCA GAG GCT GAG CAA GAG ATG CAG GAG CGA ATC AAG GCC ACG GCC ATT CGG ACA GAG
Mouse       Lys Ala Ala Glu Ala Glu Gln Glu Met Gln Glu Arg Ile Lys Ala Thr Ala Ile Arg Thr Glu  420
Human         -   -   -   -   -   -   -   -   -   -   -   -   -   -   -   -   -   -   -   -   -

Mouse  1261 GAG GAG AAG CGC CTG ATG GAG CAG CAG AAG GAG GTG CTG GAA GCT GCA TTG AAC ATG
Mouse       Glu Glu Lys Arg Leu Met Glu Gln Gln Lys Glu Val Leu Glu Ala Ala Leu Asn Met  440
Human         -   -   -   -   -   -   -   -   -   -   -   -   -   -   -   -   -   - Lys Mouse  1321 GCT GAG GAG TCA GAG GAG AGG GCC AAG GAG GCT GAT CAG TTA AAG CAA GAC TTG CAA GAA
Mouse       Ala Glu Glu Ser Glu Glu Arg Ala Lys Glu Ala Asp Gln Leu Lys Gln Asp Leu Gln Glu  460
Human         -   -   -   -   -   -   -   -   -   -   -   -   -   -   -   -   -   -   -   -

Mouse  1381 GCC AGA GAA GCA GAG CGA AGA GCC AAG CTC TTA GAA ATC GCC AAG CCC ACC
Mouse       Ala Arg Glu Ala Glu Arg Arg Ala Lys Leu Leu Glu Ile Ala Thr Lys Pro Thr  480
Human         -   -   -   -   -   -   -   -   -   -   -   -   -   -   -   -   -   -

Mouse  1441 TAT CCA CCC ATG AAC CCA ATT CCA CTG CCT CCT GAC ATA CCG AGC TTC GAC ATT
Mouse       Tyr Pro Pro Met Asn Pro Ile Pro Leu Pro Pro Asp Ile Pro Ser Phe Asp Ile  500
Human         -   -   -   -   -   -   -   -   -   - Ala   -   -   -   -   -   - Asn Leu Mouse  1501 ATT GCT GAC AGC TTG TCA TTC GAC TTC AAG GAT ACG GAC ATG AAG CAC CTG CGA ATG GAG
Mouse       Ile Ala Asp Ser Leu Ser Phe Asp Phe Lys Asp Thr Asp Met Lys His Leu Arg Met Glu  520
Human       Gly   -   -   -   -   -   -   -   -   -   -   -   -   -   -   -   -   -   -   -

Mouse  1561 ATA GAG AAA AAA GTG AAG GTG TAC ATG GAG CAC CTG CAG GAG CAG CTC AAC
Mouse       Ile Glu Lys Lys Val Lys Val Tyr Met Glu His Leu Gln Glu Gln Leu Asn  540
Human         -   -   -   -   -   -   -   -   -   -   -   -   -   -   -   -   -

Mouse  1621 GAG CTC AAG ACG GAG ATC ATC GAG GCC TTG AAA CTC AAA GAG CGG GAG ACG GCC TTG GAC GTC
Mouse       Glu Leu Lys Thr Glu Ile Ile Glu Ala Leu Lys Leu Lys Glu Arg Glu Thr Ala Leu Asp Val  560
Human         -   -   -   -   -   -   -   -   -   -   -   -   -   -   -   -   -   -   -   - Ile Mouse  1681 CTA CAC GAG AGC GAG AGC TCA GAC AGA GGG GGC CCC AGC AGC AAG CAT AAT ACC ATT AAA AAG
Mouse       Leu His Glu Ser Glu Ser Ser Asp Arg Gly Gly Pro Ser Ser Lys His Asn Thr Ile Lys Lys  580
Human         -   - Asn   - Asn   -   -   -   -   -   -   -   -   -   -   -   -   -   -   -   -

Mouse  1741 CTC ACT CTG CAG AGC GCC AAG TCC CGA GTG GCC TTC TTT GAA GAA CTC TAG caggtgacc-3'
Mouse       Leu Thr Leu Gln Ser Ala Lys Ser Arg Val Ala Phe Phe Glu Glu Leu  *
Human         -   -   -   -   -   -   -   -   -   -   -   -   -   -   -   -  *
```

FIG. 1C

```
                                              5'- gcgcccgtacctcgcg
    1 ATG GCC GGA GCC ATC GCT TCT CGC ATG AGC TCA CTC AAG AGG AAG CAG CCC AAG     20
      Met Ala Gly Ala Ile Ala Ser Arg Met Ser Phr Ser Leu Lys Arg Lys Gln Pro Lys 61 ACA TTC ACG GTG CGG ATC GTC ACC ATG GAG GCC ATG GAG TTC AAC TGC GAG ATG AAA  40
      Thr Phe Thr Val Arg Ile Val Thr Met Asp Ala Met Glu Phe Asn Cys Glu Met Lys 121 TGG AAG GGG AAG GAC CTG TTT GAT TTG GTG TGC CGG ACA CTG GGG CTT CGG GAA ACC TGG  60
      Trp Lys Gly Lys Asp Leu Phe Asp Leu Val Cys Arg Thr Leu Gly Leu Arg Glu Thr Trp 181 TTC TTT GGA CTG CAG TAT ACA ATC AAG GAC ACG GTG GCC TGG CTC AAA ATG CTC AAG AAG  80
      Phe Phe Gly Leu Gln Tyr Thr Ile Lys Asp Thr Val Ala Trp Leu Lys Met Leu Lys Lys 241 GTG TTG GAT CAT GAT GTT TCG AAG GAA GAA CCA GTT CAA GTT ACC TTT CAC TTC CTG GCC AAA TTT  100
      Val Leu Asp His Asp Val Ser Lys Glu Glu Pro Val Gln Val Thr Phe His Phe Leu Ala Lys Phe 301 TAT CCT GAA AAT GCT GAG CAG ATT TTG CTA GTT CAA GAG ATC ACG CCT CCC GAG GCG TCC CTC  120
      Tyr Pro Glu Asn Ala Glu Gln Ile Leu Val Gln Glu Ile Thr Pro Pro Glu Ala Ser Leu 361 CAG GTG AAG AAG CAG GTC GTC GAT GCT GCC AAG TAT GGC AAA CTC TGC TAT GAC CCC AAG CGG  140
      Gln Val Lys Lys Gln Val Val Asp Ala Ala Lys Tyr Gly Cys Tyr Asp Pro Lys Arg 421 TTG GCG TCA TAT TTA GCC CAA GAG GAA TTG CTC CCG AAA GCC TAT GAC CCC AAT CTC TAT CAG ATG ACT  160
      Leu Ala Ser Tyr Leu Ala Gln Glu Glu Leu Leu Pro Lys Ala Tyr Asp Pro Asn Leu Tyr Gln Met Thr 481 GGA TTT TTA GCC CAA GAG GAA TTG CTC CCG AAA GCT ACG ATT ACG GCT TGG TAT GCG GAG CAC CGG GGC GCC  180
      Gly Phe Leu Ala Gln Glu Glu Leu Leu Pro Lys Ala Thr Ile Thr Ala Trp Tyr Ala Glu His Arg Gly Ala 541 CCG GAA ATG TGG GAG AGA ATT ACG GCT TGG TAT GCG GAG CAC CGG AGA GCC AGG  200
      Pro Glu Met Trp Glu Arg Ile Thr Ala Trp Tyr Ala Glu His Arg Arg Ala Arg 601 GAT GAA GCT GAA ATG GAG GAG TAT TTG AAG ATA ATT CAG GCT CAG CTG GAG ATG TAT GGT GTG AAC  220
      Asp Glu Ala Glu Met Glu Glu Tyr Leu Lys Ile Ile Gln Ala Gln Leu Glu Met Tyr Gly Val Asn 661 TAC TTT ACA ATC CGG AAT AAA AAG GGC ACA GAG TTG CTG GGA GTG GAT GCT CTT GGG  240
      Tyr Phe Thr Ile Arg Asn Lys Lys Gly Thr Glu Leu Leu Leu Gly Val Asp Ala Leu Gly
```

FIG. 2A

```
 721 CTT CAT ATC TAT GAC CCT GAG AAC AGG CTG ACC CCC AAG ATC TCC TTC CCA TGG AAT GAA
     Leu His Ile Tyr Asp Pro Glu Asn Arg Leu Thr Pro Lys Ile Ser Phe Pro Trp Asn Glu 260

781 ATC CGA AAC ATC TCC TAC AGC GAC TAT AGC GAG TTT ACT ATT AAA CCA CTG GAT AAG AAA ATT
     Ile Arg Asn Ile Ser Tyr Ser Asp Tyr Ser Glu Phe Thr Ile Lys Pro Leu Asp Lys Lys Ile 280

841 GAT GTC TTC AAA TTT AAC TCC TCA AAG CTT CGT GTT AAT AAG CTG ATT CTT CAG CTA TGT
     Asp Val Phe Lys Phe Asn Ser Ser Lys Leu Arg Val Asn Lys Leu Ile Leu Gln Leu Cys 300

901 ATT GGG AAC CAT GAC CTA TTT ATG AGG CGA AAA GCT GAC TCT TTA GAA GTT CAG CAG
     Ile Gly Asn His Asp Leu Phe Met Arg Arg Arg Lys Ala Asp Ser Leu Glu Val Gln Gln 320

961 ATG AAA GCC CAG GCC AGG GAA GAG GAG GAG CTG AAA AAG GCT AGA AAG CAG ATG CGG AGG AGG CTC
     Met Lys Ala Gln Ala Arg Glu Glu Glu Leu Lys Ala Arg Lys Gln Met Arg Arg Arg Leu 340

1021 CGA GAG AAG CAG ATG CGG ATG GAG CGG CCG GAG GAG GCC GAG ACA AGA AGA GAT GAG TTA GAG AGG AGG CTC
     Arg Glu Lys Gln Met Arg Met Glu Arg Pro Glu Glu Ala Glu Thr Arg Arg Asp Glu Leu Glu Arg Leu 360

1081 CTG CAG AAA GAA ATG GAA GCA ACG GCC ATG GAA GAT GCT CTG CGC TCT GAG GAG ACA
     Leu Gln Lys Glu Met Glu Ala Thr Ala Met Glu Asp Ala Leu Arg Ser Glu Glu Thr 380

1141 GCT GAT CTG TTG GCT GAA GAA GCT CAG CAG ATC CGA CAG ATG CAG GAG CTT TTG GCA CAA
     Ala Asp Leu Leu Ala Glu Glu Ala Gln Gln Ile Arg Gln Met Gln Glu Leu Leu Ala Gln 400

1201 AAG CAG GAG CGC GAG ATG CGC AGG AGG AAG CAG CAG ATG CAG ATC GAA GCC ACG GCC ATT CGG ACA GAG
     Lys Gln Glu Arg Glu Met Arg Arg Arg Lys Gln Gln Met Gln Ile Glu Ala Thr Ala Ile Arg Thr Glu 420

1261 GAG GAG AAG CGC CTG CTG ATG GAG CAG CAG GTG CTG GAG GCT GAT CAG TTA AAG CAA GAC TTG AAC ATG
     Glu Glu Lys Arg Leu Leu Met Glu Gln Gln Val Leu Glu Ala Asp Gln Leu Lys Gln Asp Leu Asn Met 440

1321 GCT GAG TCA GAG GAG AGG GCC AAG AGG CTC CAA GAC TTG CAA GAA
     Ala Glu Ser Glu Glu Arg Ala Lys Arg Leu Gln Asp Leu Gln Glu 460

1381 GCC AGA GAA GCA GAG AGA GCC AAG CAG GCT CTC TTA GAA ATC GCC ACC AAG CCC ACC
     Ala Arg Glu Ala Glu Arg Ala Lys Gln Ala Leu Leu Glu Ile Ala Thr Lys Pro Thr 480
```

FIG. 2B

```
1441  TAT CCA CCC ATG AAC CCA ATT CCA CCA CTG CCT CCT GAC ATA CCG AGC TTC GAC ATT
      Tyr Pro Pro Met Asn Pro Ile Pro Pro Leu Pro Pro Asp Ile Pro Ser Phe Asp Ile 500

1501  ATT GCT GAC AGC TTG TCA TTC GAC TTC AAG GAT ACG GAC ATG ACG AAG CGA CTT TCC ATG GAG
      Ile Ala Asp Ser Leu Ser Phe Asp Phe Lys Asp Thr Asp Met Thr Lys Arg Leu Ser Met Glu 520

1561  ATA GAG AAA GAA GTG AAA TAC ATG GAG AAG CAC CTG AGC CAG GAG CAG CTC AAC
      Ile Glu Lys Glu Val Lys Tyr Met Glu Lys His Leu Ser Gln Glu Gln Leu Asn 540

1621  GAG CTC AAG ACG GAG ATC GAG GCC TTG AAA CTC CTG AAA GAG CGG ACG GCC TTG GAC GTC
      Glu Leu Lys Thr Glu Ile Glu Ala Leu Lys Leu Leu Lys Glu Arg Thr Ala Leu Asp Val 560

1681  CTA CAC AGC GAG AGC TCA GAC AGA AGC AGC AAG CAT AAT ACC ATT AAA AAG
      Leu His Ser Glu Ser Ser Asp Arg Ser Ser Lys His Asn Thr Ile Lys Lys 580

1741  CCT CAA GCC CAA GGC AGA AGA CCT ATC TGC ATT TGA GTC CTC AAA CTC ACT CTG CAG AGC
      Pro Gln Ala Gln Gly Arg Arg Pro Ile Cys Ile *** 591

1801  GCC AAG TCC CGA GTG GCC TTC TTT GAA GAA CTC TAGcaggtgacc-3'
```

FIG. 2C

```
                                          5'- gcgcccggtacctcgcg
  1 ATG GCC GGA GCC ATC GCT TCT CGC ATG AGC TTC AGC TCA CTC AAG AGG AAG CAG CCC AAG   20
    Met Ala Gly Ala Ile Ala Ser Arg Met Ser Phe Ser Ser Leu Lys Arg Lys Gln Pro Lys
 61 ACA TTC ACG GTG CGG ATC GTC ACC ATG GAG ATG GAG ATG GAG TTC AAC TGC GAG ATG AAA   40
    Thr Phe Thr Val Arg Ile Val Thr Met Asp Ala Met Glu Phe Asn Cys Glu Met Lys
121 TGG AAG GGG AAG GAC CTG TTT GAT TTG TGT GTG TGC CGG ACA CTG GGG CTT CGG GAA ACC TGG   60
    Trp Lys Gly Lys Asp Leu Phe Asp Leu Cys Val Cys Arg Thr Leu Gly Leu Arg Glu Thr Trp
181 TTC TTT GGA CTG CAG TAT ACA ATC AAG GAC GTG GCC TGG CTC AAA ATG GAC AAG AAG   80
    Phe Phe Gly Leu Gln Tyr Thr Ile Lys Asp Val Ala Trp Leu Lys Met Asp Lys Lys
241 GTG GAT CAT GAT GTT TCG AAG GAA GTT CCA ACC TTT CAC CTG GCC AAA TTT   100
    Val Asp His Asp Val Ser Lys Glu Val Pro Thr Phe His Phe Leu Ala Lys Phe
301 TAT CCT GAA AAT GCT GAG GAG ATT CAA GTT CTA GTT CAA GAG ATC ACG CAA CAC TTA TTT TTC TTA   120
    Tyr Pro Glu Asn Ala Glu Glu Ile Gln Val Leu Val Gln Glu Ile Thr Gln His Leu Phe Phe Leu
361 CAG GTG AAG AAG CAG ATT TTG GAT GAA GTC TGC CCT GAG GCG TCC GTG CTC   140
    Gln Val Lys Lys Gln Ile Leu Asp Glu Val Cys Pro Glu Ala Ser Val Leu
421 TTG GCG TCA TAT GCT GTC CAG GCC AAG TAT GGC GAC TAT GAC CCC TCT GTG CAC AAG CGG   160
    Leu Ala Ser Tyr Ala Val Gln Ala Lys Tyr Gly Asp Tyr Asp Pro Ser Val His Lys Arg
481 GGA TTT TTA GCC CAA CAG GAA GAA TTG CTC CCG AAA AGG GTG ATA AAT CTC TAT CAG ATG ACT   180
    Gly Phe Leu Ala Gln Gln Glu Glu Leu Leu Pro Lys Arg Val Ile Asn Leu Tyr Gln Met Thr
541 CCG GAA ATG TGG GAG GAG AGA ATT ACG GCT TGG TAT GCG GAG CAC CGG AGA GCC AGG   200
    Pro Glu Met Trp Glu Glu Arg Ile Thr Ala Trp Tyr Ala Glu His Arg Arg Ala Arg
601 GAT GAA GCT GAA ATG GAG TAT CAG ATA GCT CAG GAT CTG GAG ATG CTG GAT TAT GGT GTG AAC   220
    Asp Glu Ala Glu Met Glu Tyr Leu Lys Ile Ala Gln Asp Leu Glu Met Tyr Gly Val Asn
661 TAC TTT ACA ATC CGG AAT AAA AAG GGC ACA GAG TTG CTG CTT GGA GTG GAT GCT CTT GGG   240
    Tyr Phe Thr Ile Arg Asn Lys Lys Gly Thr Glu Leu Leu Leu Gly Val Asp Ala Leu Gly
```

FIG. 3A

```
721  CTT CAT ATC TAT GAC CCT GAG AAC AGG CTG ACC CCC AAG ATC TCC TTC CCA TGG AAT GAA  260
     Leu His Ile Tyr Asp Pro Glu Asn Arg Leu Thr Pro Lys Ile Ser Phe Pro Trp Asn Glu

781  ATC CGA AAC ATC TCC TAC AGC GAC GAG AAG CTG GAT AAG CCA CTG GAT AAG CCA AAA ATT  280
     Ile Arg Asn Ile Ser Tyr Ser Asp Glu Lys Leu Asp Lys Pro Leu Asp Lys Pro Lys Ile

841  GAT GTC TTC AAA TTT AAC TCC TCA AAG CTT CGT GTT AAT AAG CTG ATT CTT CAG CTA TGT  300
     Asp Val Phe Lys Phe Asn Ser Ser Lys Leu Arg Val Asn Lys Leu Ile Leu Gln Leu Cys

901  ATT GGG AAC CAT GAC CTA TTT ATG AGG CGA AAA GCT GAC TCT TTA GAA GTT CAG CAG  320
     Ile Gly Asn His Asp Leu Phe Met Arg Arg Lys Ala Asp Ser Leu Glu Val Gln Gln

961  ATG AAA GCC CAG AGG GAA GAG GAG AAG CAG AGA AAG AAG CAG CGG CTG GCT  340
     Met Lys Ala Gln Arg Glu Glu Glu Lys Gln Arg Lys Lys Gln Arg Leu Ala

1021 CGA GAG AAG CAG ATG CGG AGA GAT ACA CGT AGA GAT GAA GCT GAG AGG AGG CTC  360
     Arg Glu Lys Gln Met Arg Arg Asp Thr Arg Arg Asp Glu Ala Glu Arg Arg Leu

1081 CTG CAG ATG AAA GAA CAG ATG GCC AAT ACA ATC ACA GAG CTG ATG TCT GAG ACA  380
     Leu Gln Met Lys Glu Gln Met Ala Asn Thr Ile Thr Glu Leu Met Ser Glu Thr

1141 GCT GAT CTG TTG GCT GAA GCT CAG CAA GAG CGA ATC CAG ATG CGC CTT TTG GCA CAA  400
     Ala Asp Leu Leu Ala Glu Ala Gln Gln Glu Arg Ile Gln Met Arg Leu Leu Ala Gln

1201 AAG GAG GAG GAG AAG CAG CAG AAG GAG ATG CAG AAG GCC ACG GCC ATT CGG ACA GAG  420
     Lys Glu Glu Glu Lys Gln Gln Lys Glu Met Gln Lys Ala Thr Ala Ile Arg Thr Glu

1261 GAG GAG GAG CGC CTG ATG GAG CAG AAG CTG CTG GCT GAA GTG CTG GCA TTG AAC ATG  440
     Glu Glu Glu Arg Leu Met Glu Gln Lys Leu Leu Ala Glu Val Leu Ala Leu Asn Met

1321 GCT GAG GAG TCA GAG AGG AGG GCC AAG AGG GAT CAG TTA CAA GAC TTG CAA GAA  460
     Ala Glu Glu Ser Glu Arg Arg Ala Lys Arg Asp Gln Leu Gln Asp Leu Gln Glu

1381 GCC AGA GAA GCA GAG CGA GCC AAG CAG CTC TTA GAA ATC GCC AAG ACC CCC ACC  480
     Ala Arg Glu Ala Glu Arg Ala Lys Gln Leu Leu Glu Ile Ala Lys Thr Pro Thr
```

FIG. 3B

```
1441 TAT CCA CCC ATG AAC CCA ATT CCA CCA CTG CCT CCT GAC ATA CCG AGC TTC GAC ATT
     Tyr Pro Pro Met Asn Pro Ile Pro Pro Leu Pro Pro Asp Ile Pro Ser Phe Asp Ile 500

1501 ATT GCT GAC AGC TTG TCA TTC GAC TTC AAG GAT ACG GAC ATG AAG CGA CTT TCC ATG GAG
     Ile Ala Asp Ser Leu Ser Phe Asp Phe Lys Asp Thr Asp Met Lys Arg Leu Ser Met Glu 520

1561 ATA GAG CTC AAG GAA GTG TAC ATG AAG AGC CAC CTG CAG GAG CAG CTC AAC
     Ile Glu Leu Lys Val Glu Tyr Met Lys Ser His Leu Gln Glu Gln Leu Asn 540

1621 GAG CTC AAG ACG GAG ATC GAG GCC TTG AAA CTC CTC AAA GAG CGG GAG ACG GCC TTG GAC GTC
     Glu Leu Lys Thr Glu Ile Glu Ala Leu Lys Leu Leu Lys Glu Arg Glu Thr Ala Leu Asp Val 560

1681 CTA CAC AGC GAG AGC TCA GAC AGA CGC GGC CCC AGC AAG CAT AAT ACC ATT AAA AAG
     Leu His Ser Glu Ser Ser Asp Arg Arg Gly Pro Ser Lys His Asn Thr Ile Lys Lys 580

1741 GTA CCT GAA ATG TGA GCT CAC TCT GCA GAG CGC CAA GTC CCG AGT GGC CTT CTT TGA AGA
     Val Pro Glu Met *** 584

1801 ACT CTA Gcaggtgacc-3'
```

FIG. 3C

```
          5        10        15        20        25        30        35        40        45        50        55        60
          *                   *                   *                   *                   *                   *
ACGGCAGCCG TCAGGGACCT GCCCCCAACT CCCCTTTCCG CTCAGGCAGG GTCCTCGCGG 65        70        75        80        85        90        95       100       105       110       115       120
          *                   *                   *                   *                   *                   *
CCCATGCTGG CCGCTGGGGA CCCGCGCAGC CCAGACCGTT CCCGGGCCGG CCAGCCGGCA 125       130       135       140       145       150       155       160       165       170       175       180
          *                   *                   *                   *                   *                   *
CCATGGTGGC CCTGAGGCCT GTGCAGCAAC TCCAGGGGGG CTAAAGGGCT CAGAGTGCAG 185       190       195       200       205       210       215       220       225       230       235
          *                   *                   *                   *                   *
GCCGTGGGGC GCGAGGGTCC CGGGCCTGAG CCCCGCGCC  ATG GCC GGG GCC ATC GCT
                                            Met Ala Gly Ala Ile Ala>
                                                TRANSLATION OF N    >

240       245       250       255       260       265       270       275       280       285
    *                   *                   *                   *                   *
TCC CGC ATG AGC TTC AGC TCT CTC AAG AGG AAG CAA CCC AAG ACG TTC
Ser Arg Met Ser Phe Ser Ser Leu Lys Arg Lys Gln Pro Lys Thr Phe>
 a   a   a   a  TRANSLATION OF NF2 II  [A]  a   a   a   a       >

290       295       300       305       310       315       320       325       330
          *                   *                   *                   *
ACC GTG AGG ATC GTC ACC ATG GAC GCC GAG ATG GAG TTC AAT TGC GAG
Thr Val Arg Ile Val Thr Met Asp Ala Glu Met Glu Phe Asn Cys Glu>
 a   a   a   a  TRANSLATION OF NF2 II  [A]  a   a   a   a       >

ATG AAG TGG AAA GGG AAG GAC CTC TTT GAT TTG GTG TGC CGG ACT CTG
Met Lys Trp Lys Gly Lys Asp Leu Phe Asp Leu Val Cys Arg Thr Leu>
 a   a   a   a  TRANSLATION OF NF2 II  [A]  a   a   a   a       >

385       390       395       400       405       410       415       420       425
                *                   *                   *                   *
GGG CTC CGA GAA ACC TGG TTC TTT GGA CTG CAG TAC ACA ATC AAG GAC
Gly Leu Arg Glu Thr Trp Phe Phe Gly Leu Gln Tyr Thr Ile Lys Asp>
 a   a   a   a  TRANSLATION OF NF2 II  [A]  a   a   a   a       >

430       435       440       445       450       455       460       465       470       475
 *                   *                   *                   *                   *
ACA GTG GCC TGG CTC AAA ATG GAC AAG AAG GTA CTG GAT CAT GAT GTT
Thr Val Ala Trp Leu Lys Met Asp Lys Lys Val Leu Asp His Asp Val>
 a   a   a   a  TRANSLATION OF NF2 II  [A]  a   a   a   a       >

480       485       490       495       500       505       510       515       520       525
                *                   *                   *                   *                   *
TCA AAG GAA GAA CCA GTC ACC TTT CAC TTC TTG GCC AAA TTT TAT CCT
Ser Lys Glu Glu Pro Val Thr Phe His Phe Leu Ala Lys Phe Tyr Pro>
 a   a   a   a  TRANSLATION OF NF2 II  [A]  a   a   a   a       >

530       535       540       545       550       555       560       565       570
    *                   *                   *                   *                   *
GAG AAT GCT GAA GAG GAG CTG GTT CAG GAG ATC ACA CAA CAT TTA TTC>
Glu Asn Ala Glu Glu Glu Leu Val Gln Glu Ile Thr Gln His Leu Phe>
 a   a   a   a  TRANSLATION OF NF2 II  [A]  a   a   a   a       >

575       580       585       590       595       600       605       610       615       620
 *                   *                   *                   *                   *
TTC TTA CAG GTA AAG AAG CAG ATT TTA GAT GAA AAG ATC TAC TGC CCT
Phe Leu Gln Val Lys Lys Gln Ile Leu Asp Glu Lys Ile Tyr Cys Pro>
 a   a   a   a  TRANSLATION OF NF2 II  [A]  a   a   a   a       >
```

FIG. 7A

```
        625       630       635       640       645       650       655       660       665
                   *                   *                   *                   *
CCT GAG GCT TCT GTG CTC CTG GCT TCT TAC GCC GTC CAG GCC AAG TAT
Pro Glu Ala Ser Val Leu Leu Ala Ser Tyr Ala Val Gln Ala Lys Tyr>
     a    a    a    a    TRANSLATION OF NF2 II   [A]    a    a    a    a    >

670       675       680       685       690       695       700       705       710       715
              *                   *                   *                   *
GGT GAC TAC GAC CCC AGT GTT CAC AAG CGG GGA TTT TTG GCC CAA GAG
Gly Asp Tyr Asp Pro Ser Val His Lys Arg Gly Phe Leu Ala Gln Glu>
     a    a    a    a    TRANSLATION OF NF2 II   [A]    a    a    a    a    >

720       725       730       735       740       745       750       755       760       765
              *                   *                   *                   *
GAA TTG CTT CCA AAA AGG GTA ATA AAT CTG TAT CAG ATG ACT CCG GAA
Glu Leu Leu Pro Lys Arg Val Ile Asn Leu Tyr Gln Met Thr Pro Glu>
     a    a    a    a    TRANSLATION OF NF2 II   [A]    a    a    a    a    >

770       775       780       785       790       795       800       805       810
                    *                   *                   *                   *
ATG TGG GAG GAG AGA ATT ACT GCT TGG TAC GCA GAG CAC CGA GGC CGA
Met Trp Glu Glu Arg Ile Thr Ala Trp Tyr Ala Glu His Arg Gly Arg>
     a    a    a    a    TRANSLATION OF NF2 II   [A]    a    a    a    a    >

815       820       825       830       835       840       845       850       855       860
            *                   *                   *                   *                   *
GCC AGG GAT GAA GCT GAA ATG GAA TAT CTG AAG ATA GCT CAG GAC CTG
Ala Arg Asp Glu Ala Glu Met Glu Tyr Leu Lys Ile Ala Gln Asp Leu>
     a    a    a    a    TRANSLATION OF NF2 II   [A]    a    a    a    a    >

865       870       875       880       885       890       895       900       905
GAG ATG TAC GGT GTG AAC TAC TTT GCA ATC CGG AAT AAA AAG GGC ACA
Glu Met Tyr Gly Val Asn Tyr Phe Ala Ile Arg Asn Lys Lys Gly Thr>
     a    a    a    a    TRANSLATION OF NF2 II   [A]    a    a    a    a    >

910       915       920       925       930       935       940       945       950       955
            *                   *                   *                   *                   *
GAG CTG CTG CTT GGA GTG GAT GCC CTG GGG CTT CAC ATT TAT GAC CCT
Glu Leu Leu Leu Gly Val Asp Ala Leu Gly Leu His Ile Tyr Asp Pro>
     a    a    a    a    TRANSLATION OF NF2 II   [A]    a    a    a    a    >

960       965       970       975       980       985       990       995       1000      1005
              *                   *                   *                   *
GAG AAC AGA CTG ACC CCC AAG ATC TCC TTC CCG TGG AAT GAA ATC CGA
Glu Asn Arg Leu Thr Pro Lys Ile Ser Phe Pro Trp Asn Glu Ile Arg>
     a    a    a    a    TRANSLATION OF NF2 II   [A]    a    a    a    a    >

1010      1015      1020      1025      1030      1035      1040      1045      1050
                    *                   *                   *                   *
AAC ATC TCG TAC AGT GAC AAG GAG TTT ACT ATT AAA CCA CTG GAT AAG
Asn Ile Ser Tyr Ser Asp Lys Glu Phe Thr Ile Lys Pro Leu Asp Lys>
     a    a    a    a    TRANSLATION OF NF2 II   [A]    a    a    a    a    >

1055      1060      1065      1070      1075      1080      1085      1090      1095      1100
            *                   *                   *                   *                   *
AAA ATT GAT GTC TTC AAG TTT AAC TCC TCA AAG CTT CGT GTT AAT AAG
Lys Ile Asp Val Phe Lys Phe Asn Ser Ser Lys Leu Arg Val Asn Lys>
     a    a    a    a    TRANSLATION OF NF2 II   [A]    a    a    a    a    >

1105      1110      1115      1120      1125      1130      1135      1140      1145
              *                   *                   *                   *
CTG ATT CTC CAG CTA TGT ATC GGG AAC CAT GAT CTA TTT ATG AGG AGA
Leu Ile Leu Gln Leu Cys Ile Gly Asn His Asp Leu Phe Met Arg Arg>
     a    a    a    a    TRANSLATION OF NF2 II   [A]    a    a    a    a    >
```

FIG. 7B

```
       1150   1155   1160   1165   1170   1175   1180   1185   1190   1195
         *             *             *             *             *
       AGG AAA GCC GAT TCT TTG GAA GTT CAG CAG ATG AAA GCC CAG GCC AGG
       Arg Lys Ala Asp Ser Leu Glu Val Gln Gln Met Lys Ala Gln Ala Arg>
         a   a   a   a  TRANSLATION OF NF2 II  [A]   a   a   a   a   >

1200   1205   1210   1215   1220   1225   1230   1235   1240   1245
         *             *             *             *             *
       GAG GAG AAG GCT AGA AAG CAG ATG GAG CGG CAG CGC CTC GCT CGA GAG
       Glu Glu Lys Ala Arg Lys Gln Met Glu Arg Gln Arg Leu Ala Arg Glu>
         a   a   a   a  TRANSLATION OF NF2 II  [A]   a   a   a   a   >

1250   1255   1260   1265   1270  1275   1280   1285   1290
            *             *             *             *             *
          AAG CAG ATG AGG GAG GAG GCT GAA CGC ACG AGG GAT GAG TTG GAG AGG
          Lys Gln Met Arg Glu Glu Ala Glu Arg Thr Arg Asp Glu Leu Glu Arg>
            a   a   a   a  TRANSLATION OF NF2 II  [A]   a   a   a   a   >

1295   1300   1305   1310   1315   1320   1325   1330   1335   1340
      *             *             *             *             *
    AGG CTG CTG CAG ATG AAA GAA GAA GCA ACA ATG GCC AAC GAA GCA CTG
    Arg Leu Leu Gln Met Lys Glu Glu Ala Thr Met Ala Asn Glu Ala Leu>
      a   a   a   a  TRANSLATION OF NF2 II  [A]   a   a   a   a   >

1345   1350   1355 1360    1365   1370   1375 1380   1385
         *             *             *             *
       ATG CGG TCT GAG GAG ACA GCT GAC CTG TTG GCT GAA AAG GCC CAG ATC
       Met Arg Ser Glu Glu Thr Ala Asp Leu Leu Ala Glu Lys Ala Gln Ile>
         a   a   a   a  TRANSLATION OF NF2 II  [A]   a   a   a   a   >

1390   1395   1400   1405   1410   1415   1420   1425   1430   1435
      *             *             *             *             *
    ACC GAG GAG GAG GCA AAA CTT CTG GCC CAG AAG GCC GCA GAG GCT GAG
    Thr Glu Glu Glu Ala Lys Leu Leu Ala Gln Lys Ala Ala Glu Ala Glu>
      a   a   a   a  TRANSLATION OF NF2 II  [A]   a   a   a   a   >

1440   1445   1450   1455   1460   1465 1470   1475   1480   1485
      *             *             *             *             *
    CAG GAA ATG CAG CGC ATC AAG GCC ACA GCG ATT CGC ACG GAG GAG GAG
    Gln Glu Met Gln Arg Ile Lys Ala Thr Ala Ile Arg Thr Glu Glu Glu>
      a   a   a   a  TRANSLATION OF NF2 II  [A]   a   a   a   a   >

1490   1495   1500   1505   1510  1515   1520   1525   1530
          *             *             *             *             *
        AAG CGC CTG ATG GAG CAG AAG GTG CTG GAA GCC GAG GTG CTG GCA CTG
        Lys Arg Leu Met Glu Gln Lys Val Leu Glu Ala Glu Val Leu Ala Leu>
          a   a   a   a  TRANSLATION OF NF2 II  [A]   a   a   a   a   >

1535   1540   1545   1550   1555   1560   1565   1570   1575   1580
      *             *             *             *             *
    AAG ATG GCT GAG GAG TCA GAG AGG AGG GCC AAA GAG GCA GAT CAG CTG
    Lys Met Ala Glu Glu Ser Glu Arg Arg Ala Lys Glu Ala Asp Gln Leu>
      a   a   a   a  TRANSLATION OF NF2 II  [A]   a   a   a   a   >

1585   1590   1595   1600   1605   1610   1615   1620   1625
            *             *             *             *
          AAG CAG GAC CTG CAG GAA GCA CGC GAG GCG GAG CGA AGA GCC AAG CAG
          Lys Gln Asp Leu Gln Glu Ala Arg Glu Ala Glu Arg Arg Ala Lys Gln>
            a   a   a   a  TRANSLATION OF NF2 II  [A]   a   a   a   a   >

1630   1635   1640   1645   1650   1655   1660   1665   1670   1675
      *             *             *             *             *
    AAG CTC CTG GAG ATT GCC ACC AAG CCC ACG TAC CCG CCC ATG AAC CCA
    Lys Leu Leu Glu Ile Ala Thr Lys Pro Thr Tyr Pro Pro Met Asn Pro>
      a   a   a   a  TRANSLATION OF NF2 II  [A]   a   a   a   a   >
```

FIG. 7C

```
       1680    1685    1690   1695    1700    1705   1710    1715   1720    1725
                *               *              *             *              *
       ATT CCA GCA CCG TTG CCT CCT GAC ATA CCA AGC TTC AAC CTC ATT GGT
       Ile Pro Ala Pro Leu Pro Pro Asp Ile Pro Ser Phe Asn Leu Ile Gly>
         a   a   a   a   TRANSLATION OF NF2 II  [A]   a   a   a   a   >

1730    1735   1740    1745    1750   1755    1760    1765   1770
            *              *              *              *              *
       GAC AGC CTG TCT TTC GAC TTC AAA GAT ACT GAC ATG AAG CGG CTT TCC
       Asp Ser Leu Ser Phe Asp Phe Lys Asp Thr Asp Met Lys Arg Leu Ser>
         a   a   a   a   TRANSLATION OF NF2 II  [A]   a   a   a   a   >

1775    1780   1785    1790    1795   1800    1805    1810   1815    1820
              *              *              *              *              *
       ATG GAG ATA GAG AAA GAA AAA GTG GAA TAC ATG GAA AAG AGC AAG CAT
       Met Glu Ile Glu Lys Glu Lys Val Glu Tyr Met Glu Lys Ser Lys His>
         a   a   a   a   TRANSLATION OF NF2 II  [A]   a   a   a   a   >

1825    1830    1835    1840   1845    1850    1855    1860   1865
                *              *              *              *
       CTG CAG GAG CAG CTC AAT GAA CTC AAG ACA GAA ATC GAG GCC TTG AAA
       Leu Gln Glu Gln Leu Asn Glu Leu Lys Thr Glu Ile Glu Ala Leu Lys>
         a   a   a   a   TRANSLATION OF NF2 II  [A]   a   a   a   a   >

1870   1875    1880    1885   1890    1895    1900   1905    1910    1915
             *              *              *              *              *
       CTG AAA GAG AGG GAG ACA GCT CTG GAT ATT CTG CAC AAT GAG AAC TCC
       Leu Lys Glu Arg Glu Thr Ala Leu Asp Ile Leu His Asn Glu Asn Ser>
         a   a   a   a   TRANSLATION OF NF2 II  [A]   a   a   a   a   >

1920    1925    1930   1935    1940    1945   1950    1955    1960   1965
              *              *              *              *              *
       GAC AGG GGT GGC AGC AGC AAG CAC AAT ACC ATT AAA AAG CCT CAA GCC
       Asp Arg Gly Gly Ser Ser Lys His Asn Thr Ile Lys Lys Pro Gln Ala>
         a   a   a   a   TRANSLATION OF NF2 II  [A]   a   a   a   a   >

1970    1975   1980    1985    1990   1995 2000    2005 2010    2015 2020
                   *              *              *              *              *
       CAA GGC AGA AGA CCT ATC TGC ATT TGA GCCCTCAA ACTCACCTTG CAGAGCGCCA
       Gln Gly Arg Arg Pro Ile Cys Ile ***>
             TRANSLATION OF NF2 II  [A]   a    >

2025 2030    2035 2040    2045 2050    2055 2060    2065 2070    2075 2080
              *              *              *              *              *
       AGTCCCGAGT GGCCTTCTTT GAAGAGCTCT AGCAGGTGAC CCAGCCACCC CAGGACCTGC 2085 2090    2095 2100    2105 2110    2115 2120    2125 2130    2135 2140
              *              *              *              *              *
```

FIG. 7D

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 1817 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (iv) ANTI-SENSE: NO (vi) ORIGINAL SOURCE:
(A) ORGANISM: murine (xi) SEQUENCE DESCRIPTION: SEQ ID NO:1:

| | | | | | | |
|---|---|---|---|---|---|---|
| GCGCCCGGTA | CCTCGCGATG | GCCGGAGCCA | TCGCTTCTCG | CATGAGCTTC | AGCTCACTCA | 60 |
| AGAGGAAGCA | GCCCAAGACA | TTCACGGTGC | GGATCGTCAC | CATGGACGCC | GAGATGGAGT | 120 |
| TCAACTGCGA | GATGAAATGG | AAGGGGAAGG | ACCTGTTTGA | TTTGGTGTGC | CGGACACTGG | 180 |
| GGCTTCGGGA | AACCTGGTTC | TTTGGACTGC | AGTATACAAT | CAAGGACACG | GTGGCCTGGC | 240 |
| TCAAAATGGA | CAAGAAGGTG | TTGGATCATG | ATGTTTCGAA | GGAAGAACCA | GTTACCTTTC | 300 |
| ACTTCCTGGC | CAAATTTTAT | CCTGAAAATG | CTGAGGAGGA | GCTAGTTCAA | GAGATCACGC | 360 |
| AACACTTATT | TTTCTTACAG | GTGAAGAAGC | AGATTTTGGA | TGAAAAGGTC | TACTGCCCTC | 420 |
| CCGAGGCGTC | CGTGCTCTTG | GCGTCATATG | CTGTCCAGGC | CAAGTATGGC | GACTATGACC | 480 |
| CCTCTGTGCA | CAAGCGGGGA | TTTTTAGCCC | AAGAGGAATT | GCTCCCGAAA | AGGGTGATAA | 540 |
| ATCTCTATCA | GATGACTCCG | GAAATGTGGG | AGGAGAGAAT | TACGGCTTGG | TATGCGGAGC | 600 |
| ACCGGGGCAG | AGCCAGGGAT | GAAGCTGAAA | TGGAGTATTT | GAAGATAGCT | CAGGACCTGG | 660 |
| AGATGTATGG | TGTGAACTAC | TTTACAATCC | GGAATAAAAA | GGGCACAGAG | TTGCTGCTTG | 720 |
| GAGTGGATGC | TCTTGGGCTT | CATATCTATG | ACCCTGAGAA | CAGGCTGACC | CCCAAGATCT | 780 |
| CCTTCCCATG | GAATGAAATC | CGAAACATCT | CCTACAGCGA | CAAGGAGTTT | ACTATTAAAC | 840 |
| CACTGGATAA | GAAAATTGAT | GTCTTCAAAT | TTAACTCCTC | AAAGCTTCGT | GTTAATAAGC | 900 |
| TGATTCTTCA | GCTATGTATT | GGGAACCATG | ACCTATTTAT | GAGGCGACGG | AAAGCTGACT | 960 |
| CTTTAGAAGT | TCAGCAGATG | AAAGCCCAGG | CCAGGGAAGA | GAAGGCTAGA | AAGCAGATGG | 1020 |
| AAAGGCAGCG | GCTGGCTCGA | GAGAAGCAGA | TGCGGGAGGA | GGCCGAGCGT | ACAAGAGATG | 1080 |
| AGTTAGAGAG | GAGGCTCCTG | CAGATGAAAG | AAGAAGCAAC | GATGGCCAAT | GAAGCTCTGA | 1140 |
| TGCGCTCTGA | GGAGACAGCT | GATCTGTTGG | CTGAAAAGGC | TCAGATCACA | GAGGAGGAGG | 1200 |
| CCAAGCTTTT | GGCACAAAAG | GCTGCAGAGG | CTGAGCAAGA | GATGCAGCGA | ATCAAGGCCA | 1260 |
| CGGCCATTCG | GACAGAGGAG | GAGAAGCGCC | TGATGGAGCA | GAAGGTGCTG | GAGGCTGAAG | 1320 |
| TGCTGGCATT | GAACATGGCT | GAGGAGTCAG | AGAGGAGGGC | CAAGGAGGCT | GATCAGTTAA | 1380 |
| AGCAAGACTT | GCAAGAAGCC | AGAGAAGCAG | AGCGAAGAGC | CAAGCAGAAG | CTCTTAGAAA | 1440 |
| TCGCCACCAA | GCCCACCTAT | CCACCCATGA | ACCCAATTCC | ACCACCACTG | CCTCCTGACA | 1500 |
| TACCGAGCTT | CGACATTATT | GCTGACAGCT | TGTCATTCGA | CTTCAAGGAT | ACGGACATGA | 1560 |
| AGCGACTTTC | CATGGAGATA | GAGAAAGAAA | AAGTGGAGTA | CATGGAGAAG | AGCAAGCACC | 1620 |
| TGCAGGAGCA | GCTCAACGAG | CTCAAGACGG | AGATCGAGGC | CTTGAAACTC | AAAGAGCGGG | 1680 |
| AGACGGCCTT | GGACGTCCTA | CACAGCGAGA | GCTCAGACAG | AGGCGGCCCC | AGCAGCAAGC | 1740 |
| ATAATACCAT | TAAAAAGCTC | ACTCTGCAGA | GCGCCAAGTC | CCGAGTGGCC | TTCTTTGAAG | 1800 |
| AACTCTAGCA | GGTGACC | | | | | 1817 |

(2) INFORMATION FOR SEQ ID NO:2:

(i) SEQUENCE CHARACTERISTICS:
(A) LENGTH: 596 amino acids
(B) TYPE: amino acid
(D) TOPOLOGY: linear (ii) MOLECULE TYPE: protein ( v ) FRAGMENT TYPE: N-terminal ( v i ) ORIGINAL SOURCE:
 ( A ) ORGANISM: murine ( x i ) SEQUENCE DESCRIPTION: SEQ ID NO:2:

```
Met Ala Gly Ala Ile Ala Ser Arg Met Ser Phe Ser Ser Leu Lys Arg
 1               5                  10                  15

Lys Gln Pro Lys Thr Phe Thr Val Arg Ile Val Thr Met Asp Ala Glu
            20                  25                  30

Met Glu Phe Asn Cys Glu Met Lys Trp Lys Gly Lys Asp Leu Phe Asp
             35                  40                  45

Leu Val Cys Arg Thr Leu Gly Leu Arg Asp Thr Trp Phe Phe Gly Leu
     50                  55                  60

Gln Tyr Thr Ile Lys Asp Thr Val Ala Trp Leu Lys Met Asp Lys Lys
 65                  70                  75                  80

Val Leu Asp His Asp Val Ser Lys Glu Glu Pro Val Thr Phe His Phe
                 85                  90                  95

Leu Ala Lys Phe Tyr Pro Glu Asn Ala Glu Glu Leu Val Gln Glu
             100                 105                 110

Ile Thr Gln His Leu Phe Phe Leu Gln Val Lys Lys Gln Ile Leu Asp
             115                 120                 125

Glu Lys Val Tyr Cys Pro Pro Glu Ala Ser Val Leu Leu Ala Ser Tyr
     130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                 165                 170                 175

Tyr Gln Met Thr Pro Glu Met Trp Glu Glu Arg Ile Thr Ala Trp Tyr
             180                 185                 190

Ala Glu His Arg Gly Arg Ala Arg Asp Glu Ala Glu Met Glu Tyr Leu
             195                 200                 205

Lys Ile Ala Gln Asp Leu Glu Met Tyr Gly Val Asn Tyr Phe Thr Ile
     210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                 245                 250                 255

Pro Trp Asn Glu Ile Arg Asn Ile Ser Tyr Ser Asp Lys Glu Phe Thr
             260                 265                 270

Ile Lys Pro Leu Asp Lys Lys Ile Asp Val Phe Lys Phe Asp Ser Ser
             275                 280                 285

Lys Leu Arg Val Asn Lys Leu Ile Leu Gln Leu Cys Ile Gly Asn His
     290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
             325                 330                 335

Gln Arg Leu Ala Arg Glu Lys Gln Met Arg Glu Glu Ala Glu Arg Thr
             340                 345                 350

Arg Asp Glu Leu Glu Arg Arg Leu Gln Met Lys Glu Glu Ala Thr
             355                 360                 365

Met Ala Asn Glu Ala Leu Met Arg Ser Glu Glu Thr Ala Asp Leu Leu
             370                 375                 380

Ala Glu Lys Ala Gln Ile Thr Glu Glu Glu Ala Lys Leu Leu Ala Gln
```

```
385                     390                     395                     400

Lys  Ala  Ala  Glu  Ala  Glu  Gln  Glu  Met  Gln  Arg  Ile  Lys  Ala  Thr  Ala
                    405                     410                     415

Ile  Arg  Thr  Glu  Glu  Glu  Lys  Arg  Leu  Met  Glu  Gln  Lys  Val  Leu  Glu
                    420                     425                     430

Ala  Glu  Val  Leu  Ala  Leu  Asn  Met  Ala  Glu  Glu  Ser  Glu  Arg  Arg  Ala
                    435                     440                     445

Lys  Glu  Ala  Asp  Gln  Leu  Lys  Gln  Asp  Leu  Gln  Glu  Ala  Arg  Glu  Ala
                    450                     455                     460

Glu  Arg  Arg  Ala  Lys  Gln  Lys  Leu  Leu  Glu  Ile  Ala  Thr  Lys  Pro  Thr
465                     470                     475                     480

Tyr  Pro  Pro  Met  Asn  Pro  Ile  Pro  Pro  Leu  Pro  Pro  Asp  Ile  Pro
                    485                     490                     495

Ser  Phe  Asp  Ile  Ile  Ala  Asp  Ser  Leu  Ser  Phe  Asp  Phe  Lys  Asp  Thr
                    500                     505                     510

Asp  Met  Lys  Arg  Leu  Ser  Met  Glu  Ile  Glu  Lys  Glu  Lys  Val  Glu  Tyr
                    515                     520                     525

Met  Glu  Lys  Ser  Lys  His  Leu  Gln  Glu  Gln  Leu  Asn  Glu  Leu  Lys  Thr
                    530                     535                     540

Glu  Ile  Glu  Ala  Leu  Lys  Leu  Lys  Glu  Arg  Glu  Thr  Ala  Leu  Asp  Val
545                     550                     555                     560

Leu  His  Ser  Glu  Ser  Ser  Asp  Arg  Gly  Gly  Pro  Ser  Ser  Lys  His  Asp
                    565                     570                     575

Thr  Ile  Lys  Lys  Leu  Thr  Leu  Gln  Ser  Ala  Lys  Ser  Arg  Val  Ala  Phe
                    580                     585                     590

Phe  Glu  Glu  Leu
                    595
```

(2) INFORMATION FOR SEQ ID NO:3:

(i) SEQUENCE CHARACTERISTICS:
    (A) LENGTH: 596 amino acids
    (B) TYPE: amino acid
    (D) TOPOLOGY: linear (ii) MOLECULE TYPE: protein (v) FRAGMENT TYPE: N-terminal (vi) ORIGINAL SOURCE:
    (A) ORGANISM: Homo sapien (xi) SEQUENCE DESCRIPTION: SEQ ID NO:3:

```
Met  Ala  Gly  Ala  Ile  Ala  Ser  Arg  Met  Ser  Phe  Ser  Ser  Leu  Lys  Arg
1                   5                   10                      15

Lys  Gln  Pro  Lys  Thr  Phe  Thr  Val  Arg  Ile  Val  Thr  Met  Asp  Ala  Glu
                    20                      25                      30

Met  Glu  Phe  Asn  Cys  Glu  Met  Lys  Trp  Lys  Gly  Lys  Asp  Leu  Phe  Asp
                    35                      40                      45

Leu  Val  Cys  Arg  Thr  Leu  Gly  Leu  Arg  Glu  Thr  Trp  Phe  Phe  Gly  Leu
                    50                      55                      60

Gln  Tyr  Thr  Ile  Lys  Asp  Thr  Val  Ala  Trp  Leu  Lys  Met  Asp  Lys  Lys
65                      70                      75                      80

Val  Leu  Asp  His  Asp  Val  Ser  Lys  Glu  Glu  Pro  Val  Thr  Phe  His  Phe
                    85                      90                      95

Leu  Ala  Lys  Phe  Tyr  Pro  Glu  Asn  Ala  Glu  Glu  Glu  Leu  Val  Gln  Glu
                    100                     105                     110

Ile  Thr  Gln  His  Leu  Phe  Phe  Leu  Gln  Val  Lys  Lys  Gln  Ile  Leu  Asp
```

|     |     |     |     |     | 115 |     |     |     |     | 120 |     |     |     |     | 125 |     |     |
|-----|-----|-----|-----|-----|-----|-----|-----|-----|-----|-----|-----|-----|-----|-----|-----|-----|-----|

Glu Lys Ile Tyr Cys Pro Pro Glu Ala Ser Val Leu Leu Ala Ser Tyr
130                 135                 140

Ala Val Gln Ala Lys Tyr Gly Asp Tyr Asp Pro Ser Val His Lys Arg
145                 150                 155                 160

Gly Phe Leu Ala Gln Glu Leu Leu Pro Lys Arg Val Ile Asn Leu
                    165                 170                 175

Tyr Gln Met Thr Pro Glu Met Trp Glu Arg Ile Thr Ala Trp Tyr
                180                 185                 190

Ala Glu His Arg Gly Arg Ala Arg Asp Glu Ala Glu Met Glu Tyr Leu
                195                 200                 205

Lys Ile Ala Gln Asp Leu Glu Met Tyr Gly Val Asn Tyr Phe Ala Ile
210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                    245                 250                 255

Pro Trp Asn Glu Ile Arg Asn Ile Ser Tyr Ser Asp Lys Glu Phe Thr
                260                 265                 270

Ile Lys Pro Leu Asp Lys Lys Ile Asp Val Phe Lys Phe Asn Ser Ser
            275                 280                 285

Lys Leu Arg Val Asn Lys Leu Ile Leu Gln Leu Cys Ile Gly Asn His
            290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                    325                 330                 335

Gln Arg Leu Ala Arg Glu Lys Gln Met Arg Glu Glu Ala Glu Arg Thr
                    340                 345                 350

Arg Asp Glu Leu Glu Arg Arg Leu Leu Gln Met Lys Glu Glu Ala Thr
                355                 360                 365

Met Ala Asn Glu Ala Leu Met Arg Ser Glu Glu Thr Ala Asp Leu Leu
370                 375                 380

Ala Glu Lys Ala Gln Ile Thr Glu Glu Glu Ala Lys Leu Leu Ala Gln
385                 390                 395                 400

Lys Ala Ala Glu Ala Glu Gln Glu Met Gln Arg Ile Lys Ala Thr Ala
                    405                 410                 415

Ile Arg Thr Glu Glu Glu Lys Arg Leu Met Glu Gln Lys Val Leu Glu
                420                 425                 430

Ala Glu Val Leu Ala Leu Lys Met Ala Glu Glu Ser Glu Arg Arg Ala
            435                 440                 445

Lys Glu Ala Asp Gln Leu Lys Gln Asp Leu Gln Glu Ala Arg Glu Ala
    450                 455                 460

Glu Arg Arg Ala Lys Gln Lys Leu Leu Glu Ile Ala Thr Lys Pro Thr
465                 470                 475                 480

Tyr Pro Pro Met Asn Pro Ile Pro Ala Pro Leu Pro Pro Asp Ile Pro
                485                 490                 495

Ser Phe Asn Leu Ile Gly Asp Ser Leu Ser Phe Asp Phe Lys Asp Thr
            500                 505                 510

Asp Met Lys Arg Leu Ser Met Glu Ile Glu Lys Glu Lys Val Glu Tyr
            515                 520                 525

Met Glu Lys Ser Lys His Leu Gln Glu Gln Leu Asn Glu Leu Lys Thr
530                 535                 540

```
          Glu   Ile   Glu   Ala   Leu   Lys   Leu   Lys   Glu   Arg   Glu   Thr   Ala   Leu   Asp   Ile
          545                     550                           555                           560

Leu   His   Asn   Glu   Asn   Ser   Asp   Arg   Gly   Gly   Pro   Ser   Ser   Lys   His   Asn
                            565                           570                           575

Thr   Ile   Lys   Lys   Leu   Thr   Leu   Gln   Ser   Ala   Lys   Ser   Arg   Val   Ala   Phe
                            580                           585                           590

Phe   Glu   Glu   Leu
                      595
```

( 2 ) INFORMATION FOR SEQ ID NO:4:

( i ) SEQUENCE CHARACTERISTICS:
        ( A ) LENGTH: 1862 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: murine ( x i ) SEQUENCE DESCRIPTION: SEQ ID NO:4:

```
GCGCCCGGTA   CCTCGCGATG   GCCGGAGCCA   TCGCTTCTCG   CATGAGCTTC   AGCTCACTCA         60
AGAGGAAGCA   GCCCAAGACA   TTCACGGTGC   GGATCGTCAC   CATGGACGCC   GAGATGGAGT        120
TCAACTGCGA   GATGAAATGG   AAGGGGAAGG   ACCTGTTTGA   TTTGGTGTGC   CGGACACTGG        180
GGCTTCGGGA   AACCTGGTTC   TTTGGACTGC   AGTATACAAT   CAAGGACACG   GTGGCCTGGC        240
TCAAAATGGA   CAAGAAGGTG   TTGGATCATG   ATGTTTCGAA   GGAAGAACCA   GTTACCTTTC        300
ACTTCCTGGC   CAAATTTTAT   CCTGAAAATG   CTGAGGAGGA   GCTAGTTCAA   GAGATCACGC        360
AACACTTATT   TTTCTTACAG   GTGAAGAAGC   AGATTTTGGA   TGAAAAGGTC   TACTGCCCTC        420
CCGAGGCGTC   CGTGCTCTTG   GCGTCATATG   CTGTCCAGGC   CAAGTATGGC   GACTATGACC        480
CCTCTGTGCA   CAAGCGGGGA   TTTTTAGCCC   AAGAGGAATT   GCTCCCGAAA   AGGGTGATAA        540
ATCTCTATCA   GATGACTCCG   GAAATGTGGG   AGGAGAGAAT   TACGGCTTGG   TATGCGGAGC        600
ACCGGGGCAG   AGCCAGGGAT   GAAGCTGAAA   TGGAGTATTT   GAAGATAGCT   CAGGACCTGG        660
AGATGTATGG   TGTGAACTAC   TTTACAATCC   GGAATAAAAA   GGGCACAGAG   TTGCTGCTTG        720
GAGTGGATGC   TCTTGGGCTT   CATATCTATG   ACCCTGAGAA   CAGGCTGACC   CCCAAGATCT        780
CCTTCCCATG   GAATGAAATC   CGAAACATCT   CCTACAGCGA   CAAGGAGTTT   ACTATTAAAC        840
CACTGGATAA   GAAAATTGAT   GTCTTCAAAT   TTAACTCCTC   AAAGCTTCGT   GTTAATAAGC        900
TGATTCTTCA   GCTATGTATT   GGGAACCATG   ACCTATTTAT   GAGGCGACGG   AAAGCTGACT        960
CTTTAGAAGT   TCAGCAGATG   AAAGCCCAGG   CCAGGGAAGA   GAAGGCTAGA   AAGCAGATGG       1020
AAAGGCAGCG   GCTGGCTCGA   GAGAAGCAGA   TGCGGGAGGA   GGCCGAGCGT   ACAAGAGATG       1080
AGTTAGAGAG   GAGGCTCCTG   CAGATGAAAG   AAGAAGCAAC   GATGGCCAAT   GAAGCTCTGA       1140
TGCGCTCTGA   GGAGACAGCT   GATCTGTTGG   CTGAAAAGGC   TCAGATCACA   GAGGAGGAGG       1200
CCAAGCTTTT   GGCACAAAAG   GCTGCAGAGG   CTGAGCAAGA   GATGCAGCGA   ATCAAGGCCA       1260
CGGCCATTCG   GACAGAGGAG   GAGAAGCGCC   TGATGGAGCA   GAAGGTGCTG   GAGGCTGAAG       1320
TGCTGGCATT   GAACATGGCT   GAGGAGTCAG   AGAGGAGGGC   CAAGGAGGCT   GATCAGTTAA       1380
AGCAAGACTT   GCAAGAAGCC   AGAGAAGCAG   AGCGAAGAGC   CAAGCAGAAG   CTCTTAGAAA       1440
```

-continued

```
TCGCCACCAA GCCCACCTAT CCACCCATGA ACCCAATTCC ACCACCACTG CCTCCTGACA      1500

TACCGAGCTT CGACATTATT GCTGACAGCT TGTCATTCGA CTTCAAGGAT ACGGACATGA      1560

AGCGACTTTC CATGGAGATA GAGAAAGAAA AAGTGGAGTA CATGGAGAAG AGCAAGCACC      1620

TGCAGGAGCA GCTCAACGAG CTCAAGACGG AGATCGAGGC CTTGAAACTC AAAGAGCGGG     1680

AGACGGCCTT GGACGTCCTA CACAGCGAGA GCTCAGACAG AGGCGGCCCC AGCAGCAAGC     1740

ATAATACCAT TAAAAAGCCT CAAGCCCAAG GCAGAAGACC TATCTGCATT TGAGTCCTCA     1800

AACTCACTCT GCAGAGCGCC AAGTCCCGAG TGGCCTTCTT TGAAGAACTC TAGCAGGTGA     1860

CC                                                                    1862
```

( 2 ) INFORMATION FOR SEQ ID NO:5:

( i ) SEQUENCE CHARACTERISTICS:
        ( A ) LENGTH: 591 amino acids
        ( B ) TYPE: amino acid
        ( D ) TOPOLOGY: linear ( i i ) MOLECULE TYPE: protein ( v ) FRAGMENT TYPE: N-terminal ( v i ) ORIGINAL SOURCE:
        ( A ) ORGANISM: murine ( x i ) SEQUENCE DESCRIPTION: SEQ ID NO:5:

```
Met Ala Gly Ala Ile Ala Ser Arg Met Ser Phe Ser Ser Leu Lys Arg
 1               5                  10                  15

Lys Gln Pro Lys Thr Phe Thr Val Arg Ile Val Thr Met Asp Ala Glu
            20                  25                  30

Met Glu Phe Asn Cys Glu Met Lys Trp Lys Gly Lys Asp Leu Phe Asp
        35                  40                  45

Leu Val Cys Arg Thr Leu Gly Leu Arg Asp Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Leu Val Gln Glu
            100                 105                 110

Ile Thr Gln His Leu Phe Phe Leu Gln Val Lys Lys Gln Ile Leu Asp
        115                 120                 125

Glu Lys Val Tyr Cys Pro Pro Glu Ala Ser Val Leu Leu Ala Ser Tyr
    130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
            180                 185                 190

Ala Glu His Arg Gly Arg Ala Arg Asp Glu Ala Glu Met Glu Tyr Leu
        195                 200                 205

Lys Ile Ala Gln Asp Leu Glu Met Tyr Gly Val Asn Tyr Phe Thr Ile
    210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255
```

```
Pro  Trp  Asn  Glu  Ile  Arg  Asn  Ile  Ser  Tyr  Ser  Asp  Lys  Glu  Phe  Thr
          260                      265                     270

Ile  Lys  Pro  Leu  Asp  Lys  Ile  Asp  Val  Phe  Lys  Phe  Asp  Ser  Ser
          275                      280                     285

Lys  Leu  Arg  Val  Asn  Lys  Leu  Ile  Leu  Gln  Leu  Cys  Ile  Gly  Asn  His
          290                      295                     300

Asp  Leu  Phe  Met  Arg  Arg  Arg  Lys  Ala  Asp  Ser  Leu  Glu  Val  Gln  Gln
305                      310                     315                         320

Met  Lys  Ala  Gln  Ala  Arg  Glu  Glu  Lys  Ala  Arg  Lys  Gln  Met  Glu  Arg
                    325                      330                     335

Gln  Arg  Leu  Ala  Arg  Glu  Lys  Gln  Met  Arg  Glu  Glu  Ala  Glu  Arg  Thr
                    340                      345                     350

Arg  Asp  Glu  Leu  Glu  Arg  Arg  Leu  Leu  Gln  Met  Lys  Glu  Glu  Ala  Thr
                    355                      360                     365

Met  Ala  Asn  Glu  Ala  Leu  Met  Arg  Ser  Glu  Glu  Thr  Ala  Asp  Leu  Leu
                    370                      375                     380

Ala  Glu  Lys  Ala  Gln  Ile  Thr  Glu  Glu  Glu  Ala  Lys  Leu  Leu  Ala  Gln
385                      390                     395                         400

Lys  Ala  Ala  Glu  Ala  Glu  Gln  Glu  Met  Gln  Arg  Ile  Lys  Ala  Thr  Ala
                    405                      410                     415

Ile  Arg  Thr  Glu  Glu  Glu  Lys  Arg  Met  Glu  Gln  Lys  Val  Leu  Glu
                    420                      425                     430

Ala  Glu  Val  Leu  Ala  Leu  Asn  Met  Ala  Glu  Glu  Ser  Glu  Arg  Arg  Ala
                    435                      440                     445

Lys  Glu  Ala  Asp  Gln  Leu  Lys  Gln  Asp  Leu  Gln  Glu  Ala  Arg  Glu  Ala
          450                      455                     460

Glu  Arg  Arg  Ala  Lys  Gln  Lys  Leu  Leu  Glu  Ile  Ala  Thr  Lys  Pro  Thr
465                      470                     475                         480

Tyr  Pro  Pro  Met  Asn  Pro  Ile  Pro  Pro  Leu  Pro  Pro  Asp  Ile  Pro
                    485                      490                     495

Ser  Phe  Asp  Ile  Ile  Ala  Asp  Ser  Leu  Ser  Phe  Asp  Phe  Lys  Asp  Thr
                    500                      505                     510

Asp  Met  Lys  Arg  Leu  Ser  Met  Glu  Ile  Glu  Lys  Glu  Lys  Val  Glu  Tyr
          515                      520                     525

Met  Glu  Lys  Ser  Lys  His  Leu  Gln  Glu  Gln  Leu  Asn  Glu  Leu  Lys  Thr
          530                      535                     540

Glu  Ile  Glu  Ala  Leu  Lys  Leu  Lys  Glu  Arg  Glu  Thr  Ala  Leu  Asp  Val
545                      550                     555                         560

Leu  His  Ser  Glu  Ser  Ser  Asp  Arg  Gly  Gly  Pro  Ser  Ser  Lys  His  Asp
                    565                      570                     575

Thr  Ile  Lys  Lys  Pro  Gln  Ala  Gln  Gly  Arg  Arg  Pro  Ile  Cys  Ile
                    580                      585                     590
```

( 2 ) INFORMATION FOR SEQ ID NO:6:

( i ) SEQUENCE CHARACTERISTICS:
        ( A ) LENGTH: 1833 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

(A) ORGANISM: murine (x i) SEQUENCE DESCRIPTION: SEQ ID NO:6:

| | | | | | | |
|---|---|---|---|---|---|---|
| GCGCCCGGTA | CCTCGCGATG | GCCGGAGCCA | TCGCTTCTCG | CATGAGCTTC | AGCTCACTCA | 60 |
| AGAGGAAGCA | GCCCAAGACA | TTCACGGTGC | GGATCGTCAC | CATGGACGCC | GAGATGGAGT | 120 |
| TCAACTGCGA | GATGAAATGG | AAGGGGAAGG | ACCTGTTTGA | TTTGGTGTGC | CGGACACTGG | 180 |
| GGCTTCGGGA | AACCTGGTTC | TTTGGACTGC | AGTATACAAT | CAAGGACACG | GTGGCCTGGC | 240 |
| TCAAAATGGA | CAAGAAGGTG | TTGGATCATG | ATGTTTCGAA | GGAAGAACCA | GTTACCTTTC | 300 |
| ACTTCCTGGC | CAAATTTTAT | CCTGAAAATG | CTGAGGAGGA | GCTAGTTCAA | GAGATCACGC | 360 |
| AACACTTATT | TTTCTTACAG | GTGAAGAAGC | AGATTTTGGA | TGAAAAGGTC | TACTGCCCTC | 420 |
| CCGAGGCGTC | CGTGCTCTTG | GCGTCATATG | CTGTCCAGGC | CAAGTATGGC | GACTATGACC | 480 |
| CCTCTGTGCA | CAAGCGGGGA | TTTTTAGCCC | AAGAGGAATT | GCTCCCGAAA | AGGGTGATAA | 540 |
| ATCTCTATCA | GATGACTCCG | GAAATGTGGG | AGGAGAGAAT | TACGGCTTGG | TATGCGGAGC | 600 |
| ACCGGGGCAG | AGCCAGGGAT | GAAGCTGAAA | TGGAGTATTT | GAAGATAGCT | CAGGACCTGG | 660 |
| AGATGTATGG | TGTGAACTAC | TTTACAATCC | GGAATAAAAA | GGGCACAGAG | TTGCTGCTTG | 720 |
| GAGTGGATGC | TCTTGGGCTT | CATATCTATG | ACCCTGAGAA | CAGGCTGACC | CCCAAGATCT | 780 |
| CCTTCCCATG | GAATGAAATC | CGAAACATCT | CCTACAGCGA | CAAGGAGTTT | ACTATTAAAC | 840 |
| CACTGGATAA | GAAAATTGAT | GTCTTCAAAT | TTAACTCCTC | AAAGCTTCGT | GTTAATAAGC | 900 |
| TGATTCTTCA | GCTATGTATT | GGGAACCATG | ACCTATTTAT | GAGGCGACGG | AAAGCTGACT | 960 |
| CTTTAGAAGT | TCAGCAGATG | AAAGCCCAGG | CCAGGGAAGA | GAAGGCTAGA | AAGCAGATGG | 1020 |
| AAAGGCAGCG | GCTGGCTCGA | GAGAAGCAGA | TGCGGGAGGA | GGCCGAGCGT | ACAAGAGATG | 1080 |
| AGTTAGAGAG | GAGGCTCCTG | CAGATGAAAG | AAGAAGCAAC | GATGGCCAAT | GAAGCTCTGA | 1140 |
| TGCGCTCTGA | GGAGACAGCT | GATCTGTTGG | CTGAAAAGGC | TCAGATCACA | GAGGAGGAGG | 1200 |
| CCAAGCTTTT | GGCACAAAAG | GCTGCAGAGG | CTGAGCAAGA | GATGCAGCGA | ATCAAGGCCA | 1260 |
| CGGCCATTCG | GACAGAGGAG | GAGAAGCGCC | TGATGGAGCA | GAAGGTGCTG | GAGGCTGAAG | 1320 |
| TGCTGGCATT | GAACATGGCT | GAGGAGTCAG | AGAGGAGGGC | CAAGGAGGCT | GATCAGTTAA | 1380 |
| AGCAAGACTT | GCAAGAAGCC | AGAGAAGCAG | AGCGAAGAGC | CAAGCAGAAG | CTCTTAGAAA | 1440 |
| TCGCCACCAA | GCCCACCTAT | CCACCCATGA | ACCCAATTCC | ACCACCACTG | CCTCCTGACA | 1500 |
| TACCGAGCTT | CGACATTATT | GCTGACAGCT | TGTCATTCGA | CTTCAAGGAT | ACGGACATGA | 1560 |
| AGCGACTTTC | CATGGAGATA | GAGAAAGAAA | AAGTGGAGTA | CATGGAGAAG | AGCAAGCACC | 1620 |
| TGCAGGAGCA | GCTCAACGAG | CTCAAGACGG | AGATCGAGGC | CTTGAAACTC | AAAGAGCGGG | 1680 |
| AGACGGCCTT | GGACGTCCTA | CACAGCGAGA | GCTCAGACAG | AGGCGGCCCC | AGCAGCAAGC | 1740 |
| ATAATACCAT | TAAAAAGGTA | CCTGAAATGT | GAGCTCACTC | TGCAGAGCGC | CAAGTCCCGA | 1800 |
| GTGGCCTTCT | TTGAAGAACT | CTAGCAGGTG | ACC | | | 1833 |

(2) INFORMATION FOR SEQ ID NO:7:

(i) SEQUENCE CHARACTERISTICS:
        (A) LENGTH: 584 amino acids
        (B) TYPE: amino acid
        (D) TOPOLOGY: linear (i i) MOLECULE TYPE: protein (v) FRAGMENT TYPE: N-terminal (v i) ORIGINAL SOURCE:
        (A) ORGANISM: murine ( x i ) SEQUENCE DESCRIPTION: SEQ ID NO:7:

```
Met Ala Gly Ala Ile Ala Ser Arg Met Ser Phe Ser Ser Leu Lys Arg
 1               5                  10                  15
Lys Gln Pro Lys Thr Phe Thr Val Arg Ile Val Thr Met Asp Ala Glu
             20                  25                  30
Met Glu Phe Asn Cys Glu Met Lys Trp Lys Gly Lys Asp Leu Phe Asp
         35                  40                  45
Leu Val Cys Arg Thr Leu Gly Leu Arg Asp Thr Trp Phe Phe Gly Leu
     50                  55                  60
Gln Tyr Thr Ile Lys Asp Thr Val Ala Trp Leu Lys Met Asp Lys Lys
 65                  70                  75                  80
Val Leu Asp His Asp Val Ser Lys Glu Glu Pro Val Thr Phe His Phe
                 85                  90                  95
Leu Ala Lys Phe Tyr Pro Glu Asn Ala Glu Glu Leu Val Gln Glu
             100                 105                 110
Ile Thr Gln His Leu Phe Phe Leu Gln Val Lys Lys Glu Ile Leu Asp
             115                 120                 125
Glu Lys Val Tyr Cys Pro Pro Glu Ala Ser Val Leu Leu Ala Ser Tyr
     130                 135                 140
Ala Val Gln Ala Lys Tyr Gly Asp Tyr Asp Pro Ser Val His Lys Arg
145                 150                 155                 160
Gly Phe Leu Ala Gln Glu Glu Leu Leu Pro Lys Arg Val Ile Asn Leu
                 165                 170                 175
Tyr Gln Met Thr Pro Glu Met Trp Glu Arg Ile Thr Ala Trp Tyr
             180                 185                 190
Ala Glu His Arg Gly Arg Ala Arg Asp Glu Ala Glu Met Glu Tyr Leu
         195                 200                 205
Lys Ile Ala Gln Asp Leu Glu Met Tyr Gly Val Asn Tyr Phe Thr Ile
    210                 215                 220
Arg Asn Lys Lys Gly Thr Glu Leu Leu Leu Gly Val Asp Ala Leu Gly
225                 230                 235                 240
Leu His Ile Tyr Asp Pro Glu Asn Arg Leu Thr Pro Lys Ile Ser Phe
                 245                 250                 255
Pro Trp Asn Glu Ile Arg Asn Ile Ser Tyr Ser Asp Lys Glu Phe Thr
             260                 265                 270
Ile Lys Pro Leu Asp Lys Lys Ile Asp Val Phe Lys Phe Asp Ser Ser
         275                 280                 285
Lys Leu Arg Val Asn Lys Leu Ile Leu Gln Leu Cys Ile Gly Asn His
     290                 295                 300
Asp Leu Phe Met Arg Arg Arg Lys Ala Asp Ser Leu Glu Val Gln Gln
305                 310                 315                 320
Met Lys Ala Gln Ala Arg Glu Glu Lys Ala Arg Lys Gln Met Glu Arg
                 325                 330                 335
Gln Arg Leu Ala Arg Glu Lys Gln Met Arg Glu Glu Ala Glu Arg Thr
             340                 345                 350
Arg Asp Glu Leu Glu Arg Arg Leu Leu Gln Met Lys Glu Glu Ala Thr
         355                 360                 365
Met Ala Asn Glu Ala Leu Met Arg Ser Glu Glu Thr Ala Asp Leu Leu
     370                 375                 380
Ala Glu Lys Ala Gln Ile Thr Glu Glu Glu Ala Lys Leu Leu Ala Gln
385                 390                 395                 400
Lys Ala Ala Glu Ala Glu Gln Glu Met Gln Arg Ile Lys Ala Thr Ala
                 405                 410                 415
```

```
          Ile  Arg  Thr  Glu  Glu  Glu  Lys  Arg  Leu  Met  Glu  Gln  Lys  Val  Leu  Glu
                         420                 425                      430

Ala  Glu  Val  Leu  Ala  Leu  Asn  Met  Ala  Glu  Glu  Ser  Glu  Arg  Arg  Ala
                    435                      440                      445

Lys  Glu  Ala  Asp  Gln  Leu  Lys  Gln  Asp  Leu  Gln  Glu  Ala  Arg  Glu  Ala
               450                      455                 460

Glu  Arg  Arg  Ala  Lys  Gln  Lys  Leu  Leu  Glu  Ile  Ala  Thr  Lys  Pro  Thr
          465                      470                      475                      480

Tyr  Pro  Pro  Met  Asn  Pro  Ile  Pro  Pro  Pro  Leu  Pro  Pro  Asp  Ile  Pro
                              485                           490                 495

Ser  Phe  Asp  Ile  Ile  Ala  Asp  Ser  Leu  Ser  Phe  Asp  Phe  Lys  Asp  Thr
                         500                      505                      510

Asp  Met  Lys  Arg  Leu  Ser  Met  Glu  Ile  Glu  Lys  Glu  Lys  Val  Glu  Tyr
                    515                      520                      525

Met  Glu  Lys  Ser  Lys  His  Leu  Gln  Glu  Gln  Leu  Asn  Glu  Leu  Lys  Thr
                    530                      535                 540

Glu  Ile  Glu  Ala  Leu  Lys  Leu  Lys  Glu  Arg  Glu  Thr  Ala  Leu  Asp  Val
          545                      550                      555                      560

Leu  His  Ser  Glu  Ser  Ser  Asp  Arg  Gly  Gly  Pro  Ser  Ser  Lys  His  Asp
                              565                      570                      575

Thr  Ile  Lys  Lys  Val  Pro  Glu  Met
                         580
```

( 2 ) INFORMATION FOR SEQ ID NO:8:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapien ( x i ) SEQUENCE DESCRIPTION: SEQ ID NO:8:

```
AAGCTCACCT  TGCAGAGCGC  CAAGTCCGA  GTGGCCTTCT  TTGAAGAGCT  CTAG                54
```

( 2 ) INFORMATION FOR SEQ ID NO:9:

( i ) SEQUENCE CHARACTERISTICS:
    ( A ) LENGTH: 2080 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapien ( x i ) SEQUENCE DESCRIPTION: SEQ ID NO:9:

```
ACGGCAGCCG  TCAGGGACCT  GCCCCCAACT  CCCCTTTCCG  CTCAGGCAGG  GTCCTCGCGG        60

CCCATGCTGG  CCGCTGGGGA  CCCGCGCAGC  CCAGACCGTT  CCCGGGCCGG  CCAGCCGGCA       120
```

| | | | | | | |
|---|---|---|---|---|---|---|
| CCATGGTGGC | CCTGAGGCCT | GTGCAGCAAC | TCCAGGGGGG | CTAAAGGGCT | CAGAGTGCAG | 180 |
| GCCGTGGGGC | GCGAGGGTCC | CGGGCCTGAG | CCCCGCGCCA | TGGCCGGGGC | CATCGCTTCC | 240 |
| CGCATGAGCT | TCAGCTCTCT | CAAGAGGAAG | CAACCCAAGA | CGTTCACCGT | GAGGATCGTC | 300 |
| ACCATGGACG | CCGAGATGGA | GTTCAATTGC | GAGATGAAGT | GGAAAGGGAA | GGACCTCTTT | 360 |
| GATTTGGTGT | GCCGGACTCT | GGGGCTCCGA | GAAACCTGGT | TCTTTGGACT | GCAGTACACA | 420 |
| ATCAAGGACA | CAGTGGCCTG | GCTCAAAATG | GACAAGAAGG | TACTGGATCA | TGATGTTTCA | 480 |
| AAGGAAGAAC | CAGTCACCTT | TCACTTCTTG | GCCAAATTTT | ATCCTGAGAA | TGCTGAAGAG | 540 |
| GAGCTGGTTC | AGGAGATCAC | ACAACATTTA | TTCTTCTTAC | AGGTAAAGAA | GCAGATTTTA | 600 |
| GATGAAAAGA | TCTACTGCCC | TCCTGAGGCT | TCTGTGCTCC | TGGCTTCTTA | CGCCGTCCAG | 660 |
| GCCAAGTATG | GTGACTACGA | CCCCAGTGTT | CACAAGCGGG | GATTTTGGC | CCAAGAGGAA | 720 |
| TTGCTTCCAA | AAAGGGTAAT | AAATCTGTAT | CAGATGACTC | CGGAAATGTG | GGAGGAGAGA | 780 |
| ATTACTGCTT | GGTACGCAGA | GCACCGAGGC | CGAGCCAGGG | ATGAAGCTGA | AATGGAATAT | 840 |
| CTGAAGATAG | CTCAGGACCT | GGAGATGTAC | GGTGTGAACT | ACTTTGCAAT | CCGGAATAAA | 900 |
| AAGGGCACAG | AGCTGCTGCT | TGGAGTGGAT | GCCCTGGGGC | TTCACATTTA | TGACCCTGAG | 960 |
| AACAGACTGA | CCCCCAAGAT | CTCCTTCCCG | TGGAATGAAA | TCCGAAACAT | CTCGTACAGT | 1020 |
| GACAAGGAGT | TTACTATTAA | ACCACTGGAT | AAGAAAATTG | ATGTCTTCAA | GTTTAACTCC | 1080 |
| TCAAAGCTTC | GTGTTAATAA | GCTGATTCTC | CAGCTATGTA | TCGGGAACCA | TGATCTATTT | 1140 |
| ATGAGGAGAA | GGAAAGCCGA | TTCTTTGAA | GTTCAGCAGA | TGAAAGCCCA | GGCCAGGGAG | 1200 |
| GAGAAGGCTA | GAAAGCAGAT | GGAGCGGCAG | CGCCTCGCTC | GAGAGAAGCA | GATGAGGGAG | 1260 |
| GAGGCTGAAC | GCACGAGGGA | TGAGTTGGAG | AGGAGGCTGC | TGCAGATGAA | AGAAGAAGCA | 1320 |
| ACAATGGCCA | ACGAAGCACT | GATGCGGTCT | GAGGAGACAG | CTGACCTGTT | GGCTGAAAAG | 1380 |
| GCCCAGATCA | CCGAGGAGGA | GGCAAAACTT | CTGGCCCAGA | AGGCCGCAGA | GGCTGAGCAG | 1440 |
| GAAATGCAGC | GCATCAAGGC | CACAGCGATT | CGCACGGAGG | AGGAGAAGCG | CCTGATGGAG | 1500 |
| CAGAAGGTGC | TGGAAGCCGA | GGTGCTGGCA | CTGAAGATGG | CTGAGGAGTC | AGAGAGGAGG | 1560 |
| GCCAAAGAGG | CAGATCAGCT | GAAGCAGGAC | CTGCAGGAAG | CACGCGAGGC | GGAGCGAAGA | 1620 |
| GCCAAGCAGA | AGCTCCTGGA | GATTGCCACC | AAGCCCACGT | ACCCGCCCAT | GAACCCAATT | 1680 |
| CCAGCACCGT | TGCCTCCTGA | CATACCAAGC | TTCAACCTCA | TTGGTGACAG | CCTGTCTTTC | 1740 |
| GACTTCAAAG | ATACTGACAT | GAAGCGGCTT | TCCATGGAGA | TAGAGAAAGA | AAAAGTGGAA | 1800 |
| TACATGGAAA | AGAGCAAGCA | TCTGCAGGAG | CAGCTCAATG | AACTCAAGAC | AGAAATCGAG | 1860 |
| GCCTTGAAAC | TGAAAGAGAG | GGAGACAGCT | CTGGATATTC | TGCACAATGA | GAACTCCGAC | 1920 |
| AGGGGTGGCA | GCAGCAAGCA | CAATACCATT | AAAAAGCCTC | AAGCCCAAGG | CAGAAGACCT | 1980 |
| ATCTGCATTT | GAGCCCTCAA | ACTCACCTTG | CAGAGCGCCA | AGTCCCGAGT | GGCCTTCTTT | 2040 |
| GAAGAGCTCT | AGCAGGTGAC | CCAGCCACCC | CAGGACCTGC | | | 2080 |

( 2 ) INFORMATION FOR SEQ ID NO:10:

( i ) SEQUENCE CHARACTERISTICS:
        ( A ) LENGTH: 591 amino acids
        ( B ) TYPE: amino acid
        ( D ) TOPOLOGY: linear ( i i ) MOLECULE TYPE: protein ( v ) FRAGMENT TYPE: N-terminal ( v i ) ORIGINAL SOURCE:
        ( A ) ORGANISM: Homo sapien ( x i ) SEQUENCE DESCRIPTION: SEQ ID NO:10:

```
Met Ala Gly Ala Ile Ala Ser Arg Met Ser Phe Ser Ser Leu Lys Arg
 1               5                  10                 15
Lys Gln Pro Lys Thr Phe Thr Val Arg Ile Val Thr Met Asp Ala Glu
            20                  25                 30
Met Glu Phe Asn Cys Glu Met Lys Trp Lys Gly Lys Asp Leu Phe Asp
        35                  40                 45
Leu Val Cys Arg Thr Leu Gly Leu Arg Glu Thr Trp Phe Phe Gly Leu
    50                  55                 60
Gln Tyr Thr Ile Lys Asp Thr Val Ala Trp Leu Lys Met Asp Lys Lys
65                  70                 75                 80
Val Leu Asp His Asp Val Ser Lys Glu Glu Pro Val Thr Phe His Phe
                85                 90                  95
Leu Ala Lys Phe Tyr Pro Glu Asn Ala Glu Glu Leu Val Gln Glu
            100                105                110
Ile Thr Gln His Leu Phe Phe Leu Gln Val Lys Lys Gln Ile Leu Asp
            115                120                125
Glu Lys Ile Tyr Cys Pro Pro Glu Ala Ser Val Leu Leu Ala Ser Tyr
    130                 135                140
Ala Val Gln Ala Lys Tyr Gly Asp Tyr Asp Pro Ser Val His Lys Arg
145                 150                 155                160
Gly Phe Leu Ala Gln Glu Glu Leu Leu Pro Lys Arg Val Ile Asn Leu
                165                 170                175
Tyr Gln Met Thr Pro Glu Met Trp Glu Arg Ile Thr Ala Trp Tyr
            180                 185                190
Ala Glu His Arg Gly Arg Ala Arg Asp Glu Ala Glu Met Glu Tyr Leu
        195                 200                205
Lys Ile Ala Gln Asp Leu Glu Met Tyr Gly Val Asn Tyr Phe Ala Ile
    210                 215                220
Arg Asn Lys Lys Gly Thr Glu Leu Leu Leu Gly Val Asp Ala Leu Gly
225                 230                 235                240
Leu His Ile Tyr Asp Pro Glu Asn Arg Leu Thr Pro Lys Ile Ser Phe
                245                 250                255
Pro Trp Asn Glu Ile Arg Asn Ile Ser Tyr Ser Asp Lys Glu Phe Thr
            260                 265                270
Ile Lys Pro Leu Asp Lys Lys Ile Asp Val Phe Lys Phe Asn Ser Ser
        275                 280                285
Lys Leu Arg Val Asn Lys Leu Ile Leu Gln Leu Cys Ile Gly Asn His
    290                 295                300
Asp Leu Phe Met Arg Arg Arg Lys Ala Asp Ser Leu Glu Val Gln Gln
305                 310                 315                320
Met Lys Ala Gln Ala Arg Glu Glu Lys Ala Arg Lys Gln Met Glu Arg
                325                 330                335
Gln Arg Leu Ala Arg Glu Lys Gln Met Arg Glu Glu Ala Glu Arg Thr
            340                 345                350
Arg Asp Glu Leu Glu Arg Arg Leu Leu Gln Met Lys Glu Glu Ala Thr
        355                 360                365
Met Ala Asn Glu Ala Leu Met Arg Ser Glu Glu Thr Ala Asp Leu Leu
    370                 375                380
Ala Glu Lys Ala Gln Ile Thr Glu Glu Glu Ala Lys Leu Leu Ala Gln
385                 390                 395                400
Lys Ala Ala Glu Ala Glu Gln Glu Met Gln Arg Ile Lys Ala Thr Ala
                405                 410                415
```

```
Ile  Arg  Thr  Glu  Glu  Glu  Lys  Arg  Leu  Met  Glu  Gln  Lys  Val  Leu  Glu
               420                 425                      430

Ala  Glu  Val  Leu  Ala  Leu  Lys  Met  Ala  Glu  Glu  Ser  Glu  Arg  Arg  Ala
          435                      440                      445

Lys  Glu  Ala  Asp  Gln  Leu  Lys  Gln  Asp  Leu  Gln  Glu  Ala  Arg  Glu  Ala
     450                      455                 460

Glu  Arg  Arg  Ala  Lys  Gln  Lys  Leu  Leu  Glu  Ile  Ala  Thr  Lys  Pro  Thr
465                      470                      475                      480

Tyr  Pro  Pro  Met  Asn  Pro  Ile  Pro  Ala  Pro  Leu  Pro  Pro  Asp  Ile  Pro
                    485                      490                      495

Ser  Phe  Asn  Leu  Ile  Gly  Asp  Ser  Leu  Ser  Phe  Asp  Phe  Lys  Asp  Thr
               500                      505                 510

Asp  Met  Lys  Arg  Leu  Ser  Met  Glu  Ile  Glu  Lys  Glu  Lys  Val  Glu  Tyr
          515                      520                 525

Met  Glu  Lys  Ser  Lys  His  Leu  Gln  Glu  Gln  Leu  Asn  Glu  Leu  Lys  Thr
     530                      535                 540

Glu  Ile  Glu  Ala  Leu  Lys  Leu  Lys  Glu  Arg  Glu  Thr  Ala  Leu  Asp  Ile
545                      550                 555                           560

Leu  His  Asn  Glu  Asn  Ser  Asp  Arg  Gly  Gly  Pro  Ser  Ser  Lys  His  Asn
                    565                      570                      575

Thr  Ile  Lys  Lys  Pro  Gln  Ala  Gln  Gly  Arg  Arg  Pro  Ile  Cys  Ile
               580                      585                      590
```

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CATGGCCGGG CCATCGCTTC C                                                       21

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCTGAACCAG CTCCTCTTCA GC                                             22

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

TCAAAGGAAG AACCAGTCAC C                                                   21

( 2 ) INFORMATION FOR SEQ ID NO:14:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:14:

TCAGCTTCAT CCCTGGCTCG          20

( 2 ) INFORMATION FOR SEQ ID NO:15:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:15:

GGAGAGAATT ACTGCTTGGT AC         22

( 2 ) INFORMATION FOR SEQ ID NO:16:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:16:

CATAAATAGA TCATGGTTCC CGAT        24

( 2 ) INFORMATION FOR SEQ ID NO:17:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:17:

CCTCAAAGCT TCGTGTTAAT AAGC        24

( 2 ) INFORMATION FOR SEQ ID NO:18:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:18:

TTCCTGCTCA GCCTCTGCGG C          21

( 2 ) INFORMATION FOR SEQ ID NO:19:

( i ) SEQUENCE CHARACTERISTICS:
          ( A ) LENGTH: 22 base pairs
          ( B ) TYPE: nucleic acid (C) STRANDEDNESS: single
(D) TOPOLOGY: linear (i i) MOLECULE TYPE: cDNA (x i) SEQUENCE DESCRIPTION: SEQ ID NO:19:

GGAGGCAAAA CTTCTGGCCC AG 22

(2) INFORMATION FOR SEQ ID NO:20:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:20:

GACAGGCTGT CACCAATGAG G 21

(2) INFORMATION FOR SEQ ID NO:21:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:21:

CAATTCCAGC ACCGTTGCCT CC 22

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:22:

GGGTGGCTGG GTCACCTGCT 20

(2) INFORMATION FOR SEQ ID NO:23:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:23:

GTGGAGTACA TGGAGAA 17

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA -continued ( x i ) SEQUENCE DESCRIPTION: SEQ ID NO:24:

TCTTCAAAGA AGGCCACTCG 20

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

ACACAGCGAG AGCTCAGACA GA 22

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

GAGGACTCAA ATGCAGATAG GTCT 24

NF2 ISOFORMS

This application is a divisional of U.S. patent application Ser. No. 08/179,738, filed Jan. 10, 1994, now U.S. Pat. No. 5,578,462.

TECHNICAL FIELD

The present invention relates generally to tumor suppressor proteins. More specifically, the invention pertains to novel human and mouse NF2 transcript isoforms.

BACKGROUND OF THE INVENTION

Neurofibromatosis type 2 (NF2) is an autosomal, dominantly inherited disorder characterized by multiple tumors of the central nervous system, predominantly bilateral vestibular schwannomas (acoustic neuromas) of the eighth cranial nerve. Other disease features include cranial meningiomas, spinal nerve root schwannomas and presenile lens opacities (Martuza et al. (1988) *N. Engl. J. Med.* 318:684–688; Kaiser-Kupfer et al. (1989) *Arch. Ophthalmol.* 107:541–544; Eldridge et al. (1991) *Am. J. Hum. Genet.* 49:133 (A676)).

The gene for NF2 has been mapped in the chromosomal region 22q12 between the loci D22S1 and D22S28. Experimenters have suggested that the gene acts as a tumor suppressor and that loss or inactivation of the gene therefore results in tumorigenesis (Seizinger et al. (1986) *Nature* 322:644–647; Seizinger et al. (1987) *Science* 236:317–319; Rouleau et al. (1987) *Nature* 329:246–248; Seizinger et al. (1987) *Proc. Natl. Acad. Sci. USA* 84:5419–5423; Wertelecki et al. (1988) *N. Engl. J. Med.* 319:278–283; Rouleau et al. (1990) *Am. J. Hum. Genet.* 46:323–328; Fontaine et al. (1991) *Genomics* 10:280–283; Wolff et al. (1992) *Am. J. Hum. Genet.* 51:478–485).

Recently, a candidate human NF2 gene was cloned and identified using physical mapping and positional cloning studies (Trofatter et al. (1993) *Cell* 72:791–800; Rouleau et al. (1993) *Nature* 363:515–521). Nonoverlapping DNA deletions in the NF2 gene region from three independent NF2 families and in mRNA from a meningioma in an unrelated NF2 patient, were demonstrated (Trofatter et al., supra). Germ-line and somatic mutations were also shown in DNA of the candidate human NF2 gene from both NF2 patients and NF2-related tumors, including sporadic meningiomas and vestibular schwannomas (Rouleau et al. (1993), supra).

The above-described NF2 gene, originally reported to encode a 587 amino acid protein, is now known to code for a protein having 595 amino acids, called merlin (for moesin-ezrin-radixin like protein). (The corrected NF2 cDNA sequence has been assigned GenBank Accession no. L11353). As evident by its name, the merlin protein exhibits significant homology to the moesin, ezrin and radixin proteins which are highly conserved. These proteins appear to be mediators between plasma membrane proteins and components of the cytoskeleton which regulate cell surface structure and dynamics, as well as cytoplasmic responses to growth factors and other external stimuli (Trofatter et al. supra; Rouleau et al. supra; Luna et al. (1992) *Science* 258:955–964). Among the family members, merlin shows the most extensive homology (65%) to moesin, ezrin and radixin within a region that spans approximately 340 residues at the N-terminus of the predicted protein (Trofatter et al. supra; Rouleau et al. (1993), supra). Cloning of the candidate NF2 gene was independently confirmed by Rouleau et al., who named the NF2-encoded gene product schwannomin (Rouleau et al. (1993), supra).

The NF2 gene is expressed in multiple tissues (Trofatter et al. supra), suggesting that alterations in this gene might be involved in the development of multiple tumor types in addition to the brain neoplasms typically associated with the inherited disorder. In this regard, cytogenetic and molecular studies have implicated losses in chromosome 22q in several human neoplasms (Seizinger et al. (1991) *Cytogenet. Cell Genet.* 58:1080–1096), including breast and colon carcinomas, glioblastomas, meningiomas, pheochromocytomas and schwannomas. This indicates that the NF2 gene may constitute a tumor suppressor gene of more general importance in tumorigenesis.

One of the methods by which varient gene products are produced is alternative splicing, a process whereby multiple transcripts are produced from a single gene. These transcript isoforms encode variant proteins with differing functions. In particular, the process yields distinct mRNAs which are often tissue-specific. Thus, the same gene can encode several proteins with differing functions, in a tissue-specific manner. In this regard, it has been suggested that alternative splicing in the C-terminal region of erythrocyte protein 4.1, a member of the moesin family, may be critical for its binding to the cytoskeletal protein, spectrin, and for the mechanical integrity of the red cell membrane (Discher et al. (1993) *J. Biol. Chem.* 268:7186–7195). However, such transcript isoforms have not heretofore been identified for the NF2 gene.

DISCLOSURE OF THE INVENTION

The present invention is based on the discovery of novel transcript isoforms of the human and mouse NF2 genes. The transcript isoforms and proteins encoded thereby are useful screening agents for diagnosing NF2 disease. The isoforms can also be used to probe tissue and tumor samples for the presence of related variants. The protein products of the transcript isoforms can be administered to cancerous tissues in order to suppress tumor growth. Similarly, cDNA from the transcript isoforms may be used in gene therapy applications. Since many of the transcript isoforms are tissue and/or tumor specific, antibodies raised against the proteins are useful tumor targeting agents.

Accordingly, in one embodiment, the invention is directed to an isolated protein encoded by an NF2 gene, other than the protein encoded by human NF2 transcript isoform I as depicted in FIGS. 1A–1B (SEQ ID NO:3).

In particularly preferred embodiments, the invention is directed to the proteins encoded by mouse NF2 isoforms I, II and III, as depicted in FIGS. 1A–1B (SEQ ID NOS:1 and 2), 2 (SEQ ID NOS:4 and 5) and 3 (SEQ ID NOS:7 and 8), respectively, as well as the protein encoded by human transcript isoform II, as depicted in FIGS. 7A–7D (SEQ ID NOS:9 and 10).

In additional embodiments, the invention is directed to antibodies reactive with these proteins.

In yet other embodiments, the invention is directed to isolated NF2 transcript isoforms encoding the above proteins.

In still further embodiments, the invention is directed to nucleic acid constructs comprising:

(a) the NF2 transcript isoforms; and (b) control sequences that are operably linked to the transcript isoforms whereby the transcript isoforms can be transcribed and translated in a host cell, and wherein at least one of the control sequences is heterologous to the transcript isoform.

In other embodiments, the subject invention is directed to host cells transformed with these constructs, and methods of recombinantly producing the NF2-encoded proteins.

These and other embodiments of the subject invention will readily occur to those of ordinary skill in the art in view of the disclosure herein.

BRIEF DESCRIPTION OF THE FIGURES

FIGS. 1A–1B depict the nucleotide sequence (SEQ ID NO:1) and deduced amino acid sequence (SEQ ID NO:2) of mouse NF2 cDNA derived from mouse transcript isoform I. The putative stop codon is indicated by an asterisk. The amino acid sequence (SEQ ID NO:3) of the human merlin protein (encoded by human transcript isoform I) is also shown. Dashes indicate positions of homology.

FIG. 2 depicts the nucleotide sequence (SEQ ID NO:4) and deduced amino acid sequence (SEQ ID NO:5) of mouse NF2 cDNA derived from mouse transcript isoform II. The putative stop codon is indicated by an asterisk.

FIG. 3 depicts the nucleotide sequence (SEQ ID NO:6) and deduced amino acid sequence (SEQ ID NO:7) of mouse NF2 cDNA derived from mouse transcript isoform III. The putative stop codon is indicated by an asterisk.

FIG. 4A depicts the 3' sequence of mouse NF2 transcript isoform II (SEQ ID NO:4). FIG. 4B depicts the 3' sequence of mouse NF2 transcript isoform III (SEQ ID NO:6).

FIGS. 7A–7D show the nucleotide sequence (SEQ ID NO:9) and deduced amino acid sequence (SEQ ID NO:10) of human NF2 cDNA derived from human transcript isoform II. The 45 bp insert is boxed and the premature termination codon is marked by three asterisks.

DETAILED DESCRIPTION

Figures 4A, 4B:
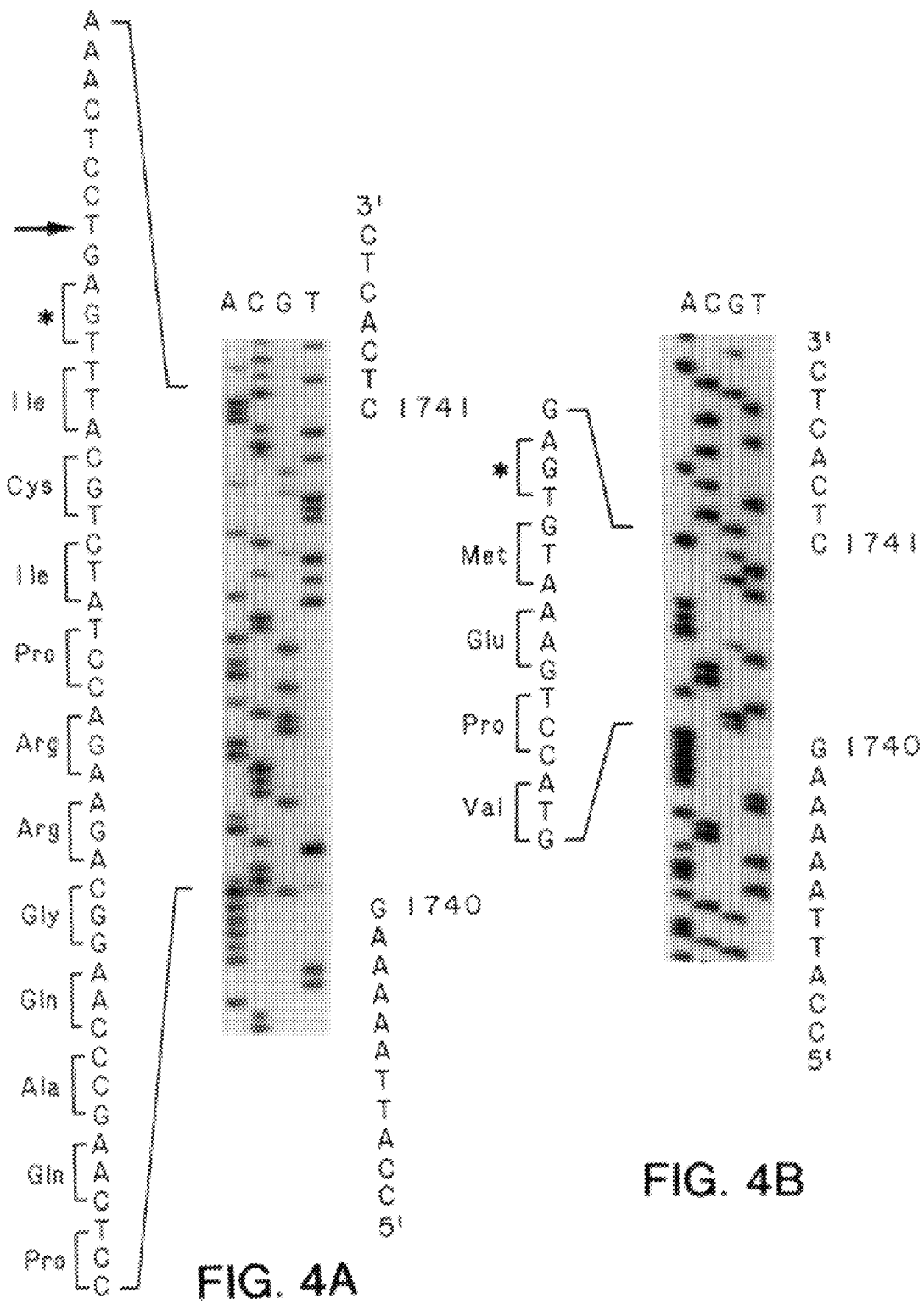
FIGS. 4A and 4B depict the partial nucleotide sequences and corresponding amino acid sequences at the 3' end of mouse NF2 transcript isoforms II (SEQ ID NOS:4 and 5) and III (SEQ ID NOS:6 and 7).

The practice of the present invention will employ, unless otherwise indicated, conventional techniques of molecular biology, microbiology and recombinant DNA technology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

By "NF2 transcript isoform" is meant a nucleic acid molecule, including DNA, RNA, mRNA, cDNA derived from the mRNA, or even synthetic DNA, which is derived either directly or indirectly from an NF2 genomic sequence. As used herein, the term specifically excludes the NF2 gene encoding the merlin protein (GenBank Accession no. L11353), described in Trofatter et al. (1993) *Cell* 72:791–800, which codes for the human protein depicted in FIG. 1 (SEQ ID NO:3), termed "human NF2 transcript isoform I" herein. The term encompasses the entire genomic sequence including introns and exons. Alternatively, a transcript isoform can include transcripts of the genomic sequences which lack one or more introns or exons, or transcripts which incorporate noncoding or coding sequences, in addition to those found in the full-length, wild-type genomic sequence. Transcript isoforms may result from naturally occurring processing of the primary transcript of a gene, or from genetic engineering of nucleotide inserts, such as additions, deletions or substitutions, to yield a distinct protein coding sequence.

Transcript isoforms may or may not code for the same protein. The protein encoded by a transcript isoform may be shorter than the protein encoded by the full-length, wild-type gene, for example, due to the presence of premature stop codons or the deletion of a length of nucleotides. Alternatively, the isoforms may code for a protein longer than the protein encoded by the full-length, wild-type gene, for example, due to an insertion of nucleotides or due to a frameshift mutation resulting from an insertion or deletion, thus shifting the location of the stop codon downstream. Furthermore, a protein product of a transcript isoform may contain amino acids which differ from the wild-type protein due to an internal insertion of coding nucleotides or due to insertion of coding nucleotides upstream or downstream from the primary transcript.

Figure 6:
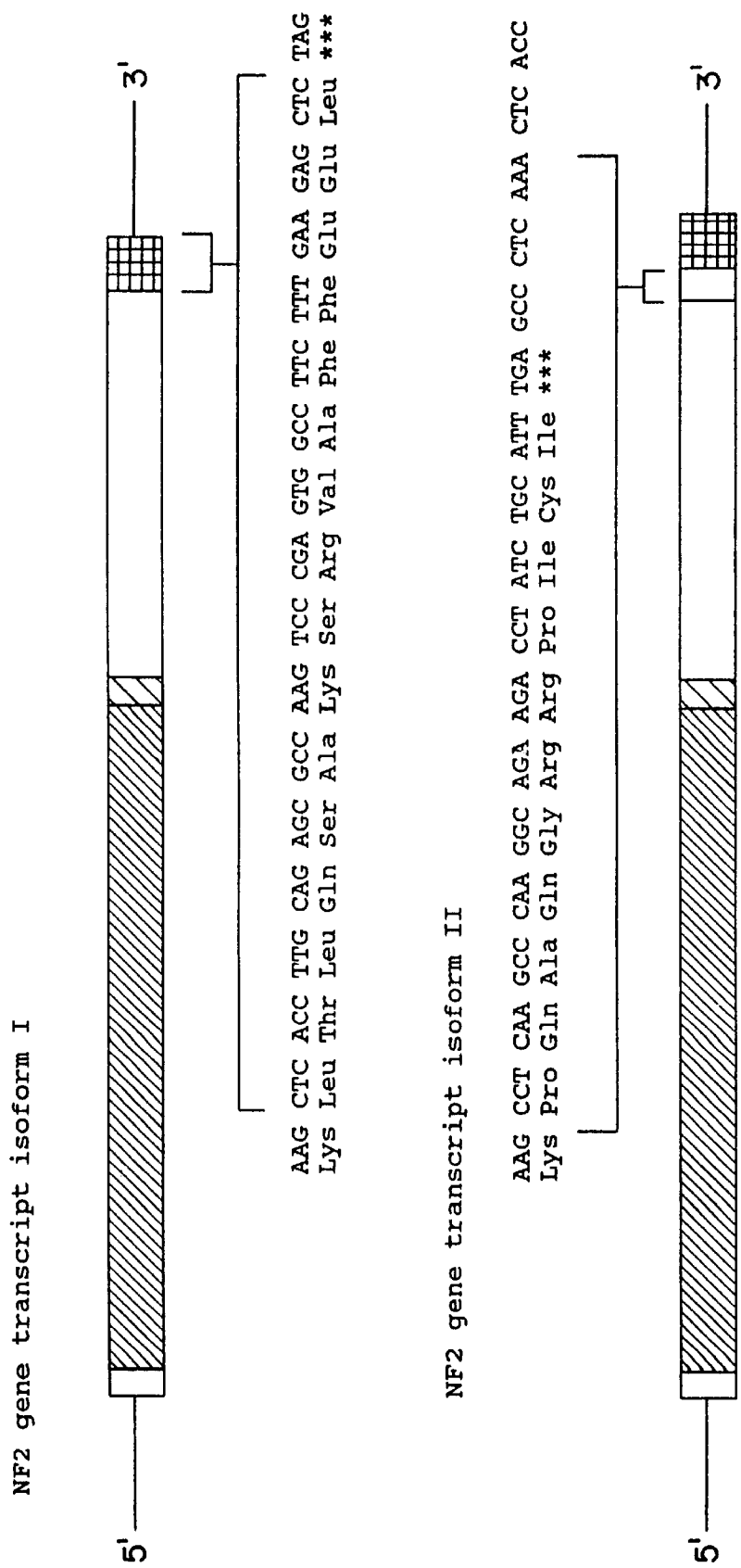
FIG. 6 shows a comparison of the partial nucleotide (SEQ ID NO:8) and predicted amino acid sequence (SEQ ID NO:3, amino acids 580 to 596) at the 3' end of human NF2 transcript isoform I and the partial nucleotide (SEQ ID NO:9, nucleotides 1954 to 2007) and predicted amino acid sequence (SEQ ID NO:10, amino acids 580 to 591) at the 3' end of human isoform II. The checkered box in isoform I indicates the nucleotide sequence encoding a variable C terminus of 16 amino acids. The black box in isoform II indicates the 45 bp insertion, and the predicted amino acid sequence, that gives rise to isoform II. Coding regions with high (densely hatched box) and partial (hatched box) homology to moesin, ezrin and radixin, are shown.

Examples of transcript isoforms include, for example, human NF2 transcript isoform II (depicted in FIGS. 6 and 7) (SEQ ID NO:9), mouse NF2 transcript isoforms I, II and III (depicted in FIGS. 1 (SEQ ID NO:1), 2 (SEQ ID NO:4) and 3 (SEQ ID NO:6), respectively), as well as nucleotide sequences substantially homologous thereto. These isoforms are described in more detail below. Thus, the term encompasses NF2 transcript isoforms derived from any mammalian species, as well as modifications, such as deletions, additions and substitutions, to these protein sequences. Such modifications of the sequences may result in proteins which have enhanced or decreased activity as compared to the wild-type sequence. These modifications may be deliberate, as through site-directed mutagenesis, or may be accidental, such as through naturally-occurring mutations. The term "transcript isoform" is used interchangeably with "alternative splice variant."

The term "NF2-encoded protein" denotes a protein encoded by an NF2 transcript isoform. Modifications to the resulting protein, such as by combination with other biological materials, such as lipids and saccharides, or by side chain modification, such as acetylation of amino groups, phosphorylation of hydroxyl side chains including phosphorylation of tyrosine, serine, threonine or any other side chains, or oxidation of sulfhydryl groups, as well as other modifications of the encoded primary sequence, are also captured by the term. Thus, included within the definition of "NF2-encoded protein" herein are glycosylated and unglycosylated forms, the amino acid sequences with or without associated phosphates, and amino acid sequences substantially homologous to the wild-type sequences.

By an "isolated protein" is meant a protein which is devoid of, in whole or part, tissue or cellular components with which the protein is normally associated in nature. Thus, a protein contained in a tissue extract would constitute an "isolated" protein, as would a protein synthetically or recombinantly produced. An "isolated" nucleotide sequence is a nucleotide sequence which has also been removed from the tissue or tumor in which it is normally found; or a sequence devoid, in whole or part, of sequences normally associated with it in nature; or a sequence, as it exists in nature, but having heterologous sequences (as defined below) in association therewith.

The term "isolated" does not denote the method by which the proteins or nucleic acid molecules are obtained or the level of purity of the preparations. Thus, such isolated species may be produced recombinantly, isolated directly from the cell or tissue of interest or produced synthetically based on the determined sequences.

Two nucleotide or polypeptide sequences are "substantially homologous" when at least about 85% (preferably at least about 85% to 90%, and most preferably at least about 95%) of the nucleotides or amino acids match over a defined length of the molecule. As used herein, substantially homologous also refers to sequences showing identity to the specified nucleotide or polypeptide sequence. Nucleotide sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The terms "polypeptide" and "protein" are used interchangeably and refer to any polymer of amino acids (dipeptide or greater) linked through peptide bonds. Thus, the terms "polypeptide" and "protein" include oligopeptides, protein fragments, analogs, muteins, fusion proteins and the like.

By "antibody reactive with an NF2-encoded protein" is meant an antibody, either polyclonal or monoclonal, which is specific for an NF2-encoded protein, as defined above, or specific for a protein homologous thereto. Such reactivity can be determined by immunoprecipitation and Western blot analysis, using methods well known in the art. Such an antibody denotes not only the intact molecule, but also active fragments thereof, retaining specificity for the NF2-encoded protein in question. (See, e.g., Baldwin, R. W. et al. in *Monoclonal Antibodies for Cancer Detection and Therapy* (Academic Press 1985) for a description of the production of antibody fragments.) The term also contemplates chimeric antibodies that retain specificity for the NF2 protein in question. In particular, the antibody can include the variable regions or fragments of the variable regions which retain specificity for the NF2-encoded molecule. The remainder of the antibody can be derived from the species in which the antibody will be used. Thus, if the antibody is to be used in a human, the antibody can be "humanized" in order to reduce immunogenicity yet retain activity. For a description of chimeric antibodies, see, e.g., Winter, G. and Milstein, C. (1991) *Nature* 349:293–299; Jones et al. (1986) *Nature* 321:522–525; Riechmann et al. (1988) 332:323–327; and Carter et al. (1992) *Proc. Natl. Acad. Sci. USA* 89:4285–4289.

"Recombinant" as used herein to describe a polynucleotide means a polynucleotide of genomic, cDNA, mRNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

A DNA "coding sequence" or a "nucleotide sequence encoding" a particular protein, is a nucleotide sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, eucaryotic mRNA, cDNA from the mRNA, genomic DNA, and even synthetic RNA and DNA sequences. A transcription termination sequence will usually be located 3' to the coding sequence.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "heterologous" region of a nucleic acid construct is an identifiable segment of nucleic acid within or attached to another nucleic acid molecule that is not found in association with the other molecule in nature. Thus, when the heterologous region encodes an NF2 isoform, the region will usually be flanked by nucleic acid that does not flank the NF2 gene in the source genome. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

B. General Methods

Central to the present invention is the discovery of several NF2 transcript isoforms, identified in a variety of tissue and tumor types. These transcript isoforms represent differential processing of genomic DNA sequences, at the level of transcription, and result in variant proteins. The isoforms provide useful tools for the analysis of the normal function of tumor suppressor factors, such as the merlin protein, and also provide useful markers for the detection of NF2 disease. Additionally, since several of the NF2-encoded proteins are present in normal, noncancerous tissues and appear to function as tumor suppressors, the protein products of the transcript isoforms can be administered to cancerous tissues in order to suppress tumor growth. Similarly, cDNA from the transcript isoforms may be used in gene therapy applications. Since many of the transcript isoforms are tissue and/or tumor specific, antibodies raised against the proteins are useful tumor targeting agents.

In particular, at least two human NF2 transcript isoforms have been identified and characterized, using RNA polymerase chain reaction (PCR) and single-strand conformational polymorphism (SSCP) analyses. These isoforms are termed "human NF2 transcript isoform I" and "human NF2 transcript isoform II," herein. Human NF2 transcript isoform I is depicted in FIGS. 1A–1B (SEQ ID NO:3). The full-length sequence of human NF2 transcript isoform I includes 1785 base pairs and encodes a protein of 595 amino acids, variously known as the merlin protein (Trofatter et al. (1993) *Cell* 72:791–800) and schwannomin (Rouleau et al. (1993) *Nature* 363:515–521). The protein was originally believed to consist of 587 amino acids (as reported in Trofatter et al. (1993) *Cell* 72:791–800). The corrected NF2 cDNA sequence has been assigned GenBank Accession No. L11353.

Human transcript isoform II carries a 45 bp insertion at nucleotide 1737, which encodes 11 amino acids and a premature termination codon, thus resulting in a variable C-terminus. The transcript encodes a putative protein of 590 amino acids. (See, FIGS. 6 and 7 (SEQ ID NO:9)).

As shown in the examples, these isoforms are expressed in multiple tissue and tumor types. Both of the human isoforms were shown to be present in several normal tissues, including heart, brain, lung, liver, skeletal muscle, kidney, pancreas and placenta, as well as in total RNA extracted from the eighth cranial nerve (the tissue from which vestibular schwannomas derive), adrenal gland and cerebellum. Human transcript isoform II appears to be present in much lower levels in the adrenal gland and the eighth cranial nerve as compared to isoform I. However, human transcript isoform II is the predominant species in RNA from the cerebellum. This novel isoform was also detected in an NF2 cDNA clone isolated from a fetal brain cDNA library. The two isoforms were also found to be present in cancerous tumors, including in glioblastoma, meningioma, and acoustic neuroma. Human transcript isoform II was also found to be expressed in three colon carcinomas, with almost complete absence of isoform I.

Mutations affecting both of the human transcript isoforms described above were detected in multiple tumor types, including sporadic vestibular schwannomas, as well as in malignant melanoma and breast carcinoma, both tumor types of which are unrelated to NF2 disease, suggesting that these NF2 transcript isoforms are generally important in tumorigenesis.

Several mouse NF2 transcript isoforms have also been identified. Exemplary transcript isoforms, termed "mouse transcript isoform I," "mouse transcript isoform II" and "mouse transcript isoform III," are described herein. The full-length coding cDNA sequence of mouse transcript isoform I is 1788 bp in length, shares 90% sequence identity with the human NF2 cDNA, and encodes a putative protein of 596 amino acids, sharing 98% homology with the protein encoded by human transcript isoform I (see FIGS. 1A–1B (SEQ ID NOS:1 and 3)). Murine transcript isoforms II and III carry a 45 bp and 16 bp insertion, respectively, at nucleotide 1740 at the 3'-end; both insertions introduce premature termination codons (see FIGS. 4A (SEQ ID NO:4) and 4B (SEQ ID NO:6)). Transcript isoforms II and III predict proteins of 591 and 584 amino acids, respectively (FIGS. 2 (SEQ ID NO:5) and 3 (SEQ ID NO:7), respectively), with altered C-termini of more hydrophilic character as compared to isoform I. Northern blot analysis and PCR analysis indicate that the mouse NF2 gene is widely expressed in different tissue types and that alternative transcripts are tissue variantly expressed. In particular, mouse transcript isoform II was shown to be more abundantly expressed than isoform I in brain, heart, liver and lung. In contrast, isoform I was the predominantly expressed species in spleen and testis. Weak but detectable expression of isoform III was observed only in spleen and testis. Although originally identified as an isolated cDNA clone from a mouse brain cDNA library, no amplification of isoform III was detected in mouse brain RNA.

Mouse transcript isoform I was obtained from a mouse brain cDNA library screened using a PCR fragment representing nearly the entire coding region of the human NF2 cDNA as a probe. Transcript isoform II was identified by reverse transcription-PCR (RT-PCR) analysis of mouse brain RNA using oligonucleotide primers flanking the insertion site at nucleotide 1740. Transcript isoform III was identified in a cDNA clone (clone λZ8).

The above-described human and mouse NF2 transcript isoforms, as well as NF2 transcript isoforms from other species, tissues and tumor types, can be conveniently identified using such techniques as PCR, SSCP, RNase cleavage, combinations of these methods, or any other techniques which are known to detect mutations at the nucleic acid level. PCR employs short oligonucleotide primers which match opposite ends of a desired sequence. The sequence between the primers need not be known. The initial template can be either RNA or DNA. If RNA is used, it is first reverse transcribed to cDNA. The cDNA is then denatured, using well known techniques, such as heat, and appropriate oligonucleotide primers are added in molar excess. Polymerization is accomplished using polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. PCR methods are described in e.g., U.S. Pat. Nos. 4,965,188; 4,800,159; 4,683,202; 4,683,195; incorporated herein by reference in their entireties.

SSCP, a method also well known in the art, makes use of differential electrophoretic mobilities resulting from conformational differences found between two short single-stranded DNA molecules. RNase cleavage similarly detects mutations at the nucleic acid level. For detecting mutations using RNase cleavage, DNA containing the sequence to be analyzed, is cloned into a vector that encodes a phage RNA polymerase. Radioactive RNA can be synthesized for use as a probe. The genomic DNA is digested using a restriction endonuclease that cleaves at sites outside of the region of interest, and this DNA is hybridized with the RNA probe. If the DNA sample contains the wild-type sequence, a perfect RNA-DNA hybrid is formed. If the DNA includes one or more mutations, the RNA-DNA hybrid contains a mismatch. At the site of the mismatch, the RNA is single-stranded. Since RNase A only cuts single-stranded RNA molecules, when the hybrid molecule is treated with this enzyme, the strand with a mismatch will be cleaved at the site and cleavage can be detected using an analytical gel. See, e.g., Myers et al. (1985) *Science* 230:1242–1246; Gibbs, R. and Caskey, C. T. (1987) *Science* 236:303–305.

Due to the conserved nature of the NF2 gene isoforms, the sequences disclosed herein can be used to design oligonucleotide probes to detect the presence of these or similar genes in other species, tissues and tumor types. In particular, genomic and cDNA libraries, derived from the desired tissue, can be prepared using techniques well known in the art. Oligonucleotide probes which contain the codons for a portion of the determined sequence can be prepared and used to screen the libraries for these and homologous NF2 genes. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert indeed contains an NF2 gene and the gene can be isolated. See, e.g., Sambrook et al., supra.

If desired, the DNA sequence can be prepared synthetically using techniques known in the art. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been synthesized or isolated, they can be cloned into any suitable vector for expression. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B. Perbal, supra. Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

The gene can be placed under the control of a promoter, ribosome binding site (for bacterial expression) and, optionally, an operator (collectively referred to herein as "control" elements), so that the DNA sequence encoding the desired NF2 protein is transcribed into RNA in the host cell transformed by a vector containing this expression construction. The coding sequence may or may not contain a signal peptide or leader sequence. Heterologous leader sequences can be added to the coding sequence which cause the secretion of the expressed polypeptide from the host organism. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the NF2 protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus spp.*, will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis,*

*Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. The proteins may also be expressed in Trypanosomes.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by HPLC. Other methods of amino acid sequencing are also known in the art.

The NF2-encoded proteins of the present invention may also be produced by chemical synthesis such as solid phase peptide synthesis, using known amino acid sequences or amino acid sequences derived from the DNA sequence of the genes of interest. Such methods are known to those skilled in the art.

Once produced, the NF2 proteins can be used in pharmaceutical compositions to ameliorate NF2 disease or tumors associated with NF2 mutations. The NF2-encoded proteins of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration, to the tumor in question, will also find use with the present invention.

Therapeutically effective doses will be easily determined by one of skill in the art and will depend on the severity and course of the disease, the patient's health and response to treatment, and the judgment of the treating physician.

An alternative route of administration involves gene therapy. Thus, the NF2 transcript isoforms (and accompanying regulatory elements) can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. *Science* (1990) 247:1465–1468). Liposome-mediated gene transfer can also be accomplished using known methods. See, e.g., Hazinski et al. *Am. J. Respir. Cell Mol. Biol.* (1991) 4:206–209; Brigham et al. *Am. J. Med. Sci.* (1989) 298:278–281; Canonico et al. *Clin. Res.* (1991) 39:219A; and Nabel et al. *Science* (1990) 249:1285–1288. Targeting agents, such as antibodies directed against surface antigens expressed on specific cell types, can be covalently conjugated to the liposomal surface so that the nucleic acid can be delivered to specific tissues and tumor types.

The NF2-encoded proteins of the present invention or their fragments can also be used to produce antibodies, both polyclonal and monoclonal. If polyclonal antibodies are desired, a selected mammal, (e.g., mouse, rabbit, goat, horse, pig etc.) is immunized with an antigen of the present invention, or its fragment, or a mutated antigen. Serum from the immunized animal is collected and treated according to known procedures. If serum containing polyclonal antibodies is used, the polyclonal antibodies can be purified by a variety of methods, such as by immunoaffinity chromatography, using known procedures.

Monoclonal antibodies to the NF2 proteins, and to the fragments thereof, can also be readily produced by one skilled in the art using, e.g., hybridoma technology. The general methodology for making monoclonal antibodies by using hybridoma technology is well known. For example, immortal antibody-producing cell lines can be created by cell fusion, as well as by other techniques such as direct transformation of B lymphocytes with oncogenic DNA, or transfection with Epstein-Barr virus. See, e.g., M. Schreier et al. *Hybridoma Techniques* (1980); Hammerling et al. *Monoclonal Antibodies and T-cell Hybridomas* (1981); Kennett et al. *Monoclonal Antibodies* (1980); U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the NF2 proteins can be screened for various properties; i.e., for isotype, epitope, affinity, etc.

The antibodies generated against the NF2-encoded proteins can be used in standard immunoassays, as diagnostic reagents, to screen tissues and/or tumors for the presence or absence of the proteins, or for the presence or absence of aberrant NF2 proteins, allowing for identification of individuals with NF2 disease, as well for the identification of carriers of the disease and the determination of individuals likely to develop NF2 disease. For example, the presence of NF2 proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the NF2 proteins and the antibodies described above.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like. Typically, the solid support is first reacted with the biological sample, washed and then the antibodies are applied. If a sandwich type format is desired, such as a sandwich ELISA assay, a commercially available anti-immunoglobulin (i.e. anti-rabbit immunoglobulin) conjugated to a detectable label, such as horseradish peroxidase, alkaline phosphatase or urease, can be added. An appropriate substrate is then used to develop a color reaction.

Alternatively, a "two antibody sandwich" assay can be used to detect both aberrant and wild-type NF2 proteins. In this technique, the solid support is reacted first with one or more of the antibodies, washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the NF2 proteins and antibodies thereto form complexes under precipitating conditions. The precipitated complexes can then be separated from the test sample, for example, by centrifugation. The reaction mixture can be analyzed to determine the presence or absence of antibody-NF2 complexes using any of a number of standard methods, such as those immunodiagnostic methods described above.

The NF2 proteins and antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental Methods

Northern analysis. A Northern blot (Clontech Laboratories, Inc.) containing 2 $\mu$g of poly A+ RNA from eight human tissues, or multiple murine tissues, was hybridized to a [$\alpha$-$^{32}$P] dCTP-labeled probe generated by reverse transcription-PCR amplification (RT-PCR) of the entire NF2 coding region. Filter hybridization was performed at 68° C. for 3 h using the Quickhyb™ solution (Stratagene, La Jolla, Calif.), followed by two washes with 2×standard saline citrate (SSC) (1×SSC=0.15M NaCl, 0.015M sodium citrate) /0.1 sodium dodecyl sulfate (SDS) for 15 min at room temperature, and one wash with 0.1×SSC/0.1% SDS for 15 min at 54° C.

Reverse Transcription-PCR (RT-PCR) Amplification. Total RNA was extracted from frozen human tumor specimens or murine tissues by lysis in guanidium thiocyanate and extraction with phenol-chloroform as described in Chomczynski et al. (1987) *Anal. Biochem.* 162:156–158. Total RNA was denatured by heating to 70° C. for 10 min in 13 $\mu$l of DEPC-treated water. After chilling on ice for 2 min, single-stranded cDNA was synthesized by incubating the denatured RNA in 20 $\mu$l 20 mM Tris-HCl (pH 8.4), 50 mM KCl, 2.5 mM MgCl$_2$, 100 ng/$\mu$l bovine serum albumin (BSA), 500 $\mu$M dNTP, 10 mM dithiothreitol (DTT), 12 ng/$\mu$l of primer 3m3 or 3m6 (tumor specimen extracts) or the specific primer 3AS1 (complementary to the 3' end of the mouse NF2 mRNA) and 5m9 (murine tissue extracts), and 200 U of SuperScript™ (Gibco BRL) reverse transcriptase for 10 min at room temperature followed by 60 min at 42° C. The reaction was terminated by heating to 95° C. for 2 min and quenching on ice. A first amplification by polymerase chain reaction (PCR) was performed using 2 $\mu$l of the reverse-transcribed product in a final volume of 100 $\mu$l such that final concentrations were 20 mM Tris-HCl (pH 8.2), 10 mM KCl, 6 mM (NH$_4$)$_2$SO$_4$ 1,5 mM MgCl$_2$, 0.1% Triton X-100, 2.5 U Pfu DNA polymerase (Stratagene), 200 $\mu$M each deoxynucleoside triphosphate, and 0.3 pmole/$\mu$l of primers 5m1 and 3m3 (for the 3m3-primed first strand cDNA) or 5m4 and 3m6 (for the 3m6-primed product) (tumor specimen extracts) or 3AS1 and 5AS1 (murine tissue extracts). Nested PCR amplifications were performed using 1 $\mu$l of first amplification product in a final volume of 100 $\mu$l (tumor specimen extracts) or 50 $\mu$l (murine tissue extracts) of solution containing 10 mM Tris-HCl (pH 8.3), 50 mM KCl, 1.5 mM MgCl$_2$, 0.001% (tumor specimen extracts) or 0.01% (murine tissue extracts) (w/v) gelatin, 200 $\mu$M (tumor specimen extracts) or 250 $\mu$M (murine tissue extracts) each deoxynucleoside triphosphate, 0.3 pmole/$\mu$l of appropriate primers, and 2.5 U Taq polymerase (Boehringer Mannheim). 30–32 cycles of amplification were performed in a Gene-Amp 9600 machine (Perkin Elmer), with denaturation at 94° C. for 15 sec, annealing at 58° C. for 15 sec, and elongation at 72° C. for 1 min and 15 sec. Final extension was at 72° C. for 3 min (murine tissue extracts). The oligonucleotide primers used in reverse transcription and PCR amplification were as follows:

5m1: 5'-CATGGCCGGGCCATCGCTTCC-3' (SEQ ID NO:11);
3m1: 5'-CCTGAACCAGCTCCTCTTCAGC-3' (SEQ ID NO:12);
5m2: 5'-TCAAAGGAAGAACCAGTCACC-3' (SEQ ID NO:13);
3m2: 5'-TCAGCTTCATCCCTGGCTCG-3' (SEQ ID NO:14);
5m3: 5'-GGAGAGAATTACTGCTTGGT AC-3' (SEQ ID NO:15);
3m3: 5'-CATAAATAGATCATGGTTCCCGAT-3' (SEQ ID NO:16);
5m4: 5'-CCTCAAAGCTTCGTGTTAATAAGC-3' (SEQ ID NO:17);
3m4: 5'-TTCCTGCTCAGCCTCTGCGGC-3' (SEQ ID NO:18);
5m5: 5'-GGAGGCAAAACTTCTGGCCCAG-3' (SEQ ID NO:19);
3m5: 5'-GACAGGCTGTCACCAATGAGG-3' (SEQ ID NO:20);
5m6: 5'-CAATTCCAGCACCGTTGCCTCC-3' (SEQ ID NO:21);
3m6: 5'-GGGTGGCTGGGTCACCTGCT-3' (SEQ ID NO:22);
5m9: 5'-GTGGAGTACATGGAGAA-3' (SEQ ID NO:23) (extending from nucleotide 1576 with respect to the full length mouse NF2 cDNA);
3AS1: 5'-TCTTCAAAGAAGGCCACTCG-3' (SEQ ID NO:24);
5AS1: 5'-ACACAGCGAGAGCTCAGACAGA-3' (SEQ ID NO:25) (extending from nucleotide 1684 with respect to the full length mouse NF2 cDNA).

Tumor samples listed in Table 1 were amplified by RNA PCR using the following oligonucleotide primer sets:

AN54: 5m1-3m1; AN10, AN13, AN72, AN26, 95540: 5m2-3m2; AN94, 86336, 90021: 5m3-3m3; AN825, 94771: 5m4-3m4; 86-20: 5m4-3m5; AN11, 87506, 95783: 5m5-3m6.

Single Strand Conformational Polymorphism (SSCP) Analysis. Nested PCR amplifications were performed for SSCP analysis using the following reaction mixture (final volume 50 µl): 1 µl of PCR-amplified template, 10 mM Tris-HCl (pH 8.3), 50 mM KCl, 1.5 mM MgCl$_2$, 0.001% (w/v) gelatin, 200 µM of each dCTP, dGTP, dTTP, 20 µM dATP, 0.1 µl of [α-$^{33}$P] dATP (3000 Ci/mmol) (Du Pont NEN), 0.3 pmole/µl of appropriate primers, and 1.25 U Taq polymerase. Following amplification, PCR products were diluted (1:10) with 0.1% SDS/10 mM EDTA. A 5 µl sample of the diluted reaction was then mixed with 6 µl of gel loading dye (U.S. Biochemical Corporation). Samples were heat denatured at 94° C. for 2 min, chilled on ice, and 3 µl loaded onto a 0.5× MDE gel (J. T. Baker, Inc.). Gels were electrophoresed at 8 watts constant power for 14 hours at room temperature using 0.6× Tris borate EDTA (TBE) buffer. After electrophoresis, gels were transferred to blotting paper, dried and subjected to autoradiography.

Genomic DNA PCR analysis. Genomic DNA extracted from the patients' blood was analyzed by PCR using oligonucleotide primers that flank the exon-intron junctions of the NF2 gene.

Sequence analysis. Individual bands were carefully excised from agarose gels or from dried SSCP gels, placed into 100 µl of deionized water, and the DNA allowed to elute for 4–6 hr at room temperature with gentle shaking. 10 µl of eluted DNA was reamplified using appropriate primers as described above. Amplified products were subcloned into the plasmid vector pCR™ II (Invitrogen Corp.), and inserts were sequenced using double-stranded recombinant plasmids as template for the dideoxy chain termination method as described in Sanger et al. (1977) *Proc. Natl. Acad. Sci. USA* 74:5463–5467. Reaction products were electrophoresed on 6% polyacrylamide, 8M urea, 0.1M Tris-borate (pH 8.3), 2 mM EDTA gels. Some of the clones were sequenced by dideoxy termination chemistry using an Applied Biosystems 373-A automated DNA sequencer. Double strand sequencing of three clones was performed for each mutant sample. Sequence data was analyzed using the MacVector™ 4.1 software (International Biotechnologies, Inc.).

Cloning of Mouse NF2 cDNAs. A mouse brain oligo (dT) and random-primed cDNA library in λZAPII (Stratagene) was screened by plaque hybridization to 10$^6$ filter-immobilized cDNA phage clones at a density of 5×10$^4$ plaque forming units (pfu)/150-mm filter. A $^{32}$P-labeled (Feinberg et al. (1983) *Anal. Biochem.* 132:266–267) PCR fragment representing nearly the entire coding region of the human NF2 cDNA (nucleotides 219 to 2031, as numbered in Trofatter et al. (1993) *Cell* 72:791–800) was used as a probe.

Prehybridization was performed at 65° C. for 3 hr in 4×standard sodium phosphate EDTA (SSPE) (1×SSPE= 0.15M NaCl, 0.010M NaH$_2$PO4.H$_2$O, 0.001M EDTA-Na$_2$, pH 7.4), 6% polyethylene glycol 8000, 0.5% sodium dodecyl sulfate, 2×Denhardt's solution and 100 mg/ml denatured sheared salmon sperm DNA. Hybridization was then carried out at 65° C. in the same solution containing radiolabeled probe. Washes were performed under high stringency. Filters were exposed overnight to Kodak X-AR films at −80° C. with intensifying screens. After 3 rounds of screening, cDNAs were rescued as pBluescript SK-phagemids (Stratogene) by in vivo excision using the R408 helper phage.

The nucleotide sequences of recombinant clones of mouse NF2 cDNAs were determined by the dideoxy chain termination method, as described above, using Sequenase version 2.0 (US Biochemical, Cleveland, Ohio). Both strands were sequenced and analyzed using MacVector™ 4.1 software.

EXAMPLE I

Cloning of Murine NF2 Transcript Isoform I Gene

In order to clone and characterize the mouse NF2 gene, a murine NF2 cDNA homolog was isolated as follows. A mouse brain cDNA library in λZAPII was screened with the $^{32}$P-labeled DNA probe spanning nearly the entire human NF2 gene coding region. Twelve positive plaques were analyzed in more detail and helper phage-rescued phagemids (pBluescript) tested for insert size after the third round of screening. Four clones with inserts of 2.0 kb, 0.8 kb, 3.5 kb and 2.0 kb were overlapping clones that cover the entire coding region of the mouse NF2 gene. The complete nucleotide and deduced amino acid sequences of the mouse NF2 cDNA, as derived from sequence analysis of both strands of these clones, are shown in FIGS. 1A–1B (SEQ ID NOS:1 and 2). The coding region consists of 1788 nucleotides, encoding a predicted protein of 596 amino acids with a calculated molecular mass of 69–70 kDa, as compared to 595 amino acids for the human protein. The one residue difference is based on the presence of a three base insertion (CCC) at nucleotide 1710, introducing a proline at this site. Sequence analysis of all isolated cDNA clones, and RT-PCR products derived from mouse brain RNA, revealed the presence of this proline, indicating that this residue is specific to the predicted mouse merlin protein. This was confirmed by sequencing of genomic DNA, which revealed that the 3 bp insertion does not represent a distinct exon in the mouse.

The overall homology of mouse and human NF2 cDNAs is 90% at the nucleotide level (a total of 172 bp substitutions) and 98% at the deduced amino acid level (a total of 10 substitutions, 7 of which constitute conservative changes and 2 of which represent semi-conservative changes). These substitutions are clustered toward the C-terminus of the predicted protein.

EXAMPLE II

Identification of Transcript Isoforms in Murine Brain

Alternative transcript isoforms of the mouse NF2 gene were identified in several of the cDNA clones described in Example I. Clone λZ8 showed an insertion of 16 bp at nucleotide 1740 (see FIG. 4B (SEQ ID NO:6)). In order to determine whether the 45 bp insertion in the alternative transcript isoform detected in the human NF2 gene (see Example VII) was also expressed in murine tissue, RT-PCR was performed on murine brain RNA using oligonucleotide primers flanking the insertion site at nucleotide 1740. Two PCR products were identified by agarose gel electrophoresis. Sequencing of the largest PCR product revealed the presence of a 45 bp insertion at nucleotide 1740, which was identical in sequence to that described for the human NF2 transcript except for one bp difference (FIG. 4A (SEQ ID NO:4), see arrow).

In concordance with the numbering system used for the human transcript variants, the mouse transcript with the 45 bp insertion was designated as isoform II, while the mouse transcript with the 16 bp insertion was designated as isoform III. The 45 bp insertion in transcript isoform II encoded 11 amino acids in frame and introduced a premature stop codon, predicting a protein of 591 amino acids. The 16 bp insertion in transcript isoform III encoded 4 amino acids in frame before introducing a premature stop codon, and thus encoded a putative protein of 584 amino acids.

EXAMPLE III

Modes of Splicing Giving Rise to Murine Transcript Isoforms

In order to determine the mechanisms by which the murine NF2 transcript isoforms arise, exon-intron boundary information was obtained as follows. Mouse genomic DNA harboring the 3' end of the mouse NF2 gene was analyzed. PCR was used to amplify mouse genomic DNA across the region from nucleotide 1684 (primer 5AS1) and the 45 bp sequence present in isoform II (antisense primer II-3': 5'-GAGGACTCAAATGCAGATAGGTCT-3' (SEQ ID NO:26)). The size of the amplified DNA fragment was about 1.5 kb. The fragment was subcloned and subjected to sequence analysis. Sequence analysis was performed with primers 5AS1 and II-3' in order to determine the exon-intron boundaries.

Figure 5:
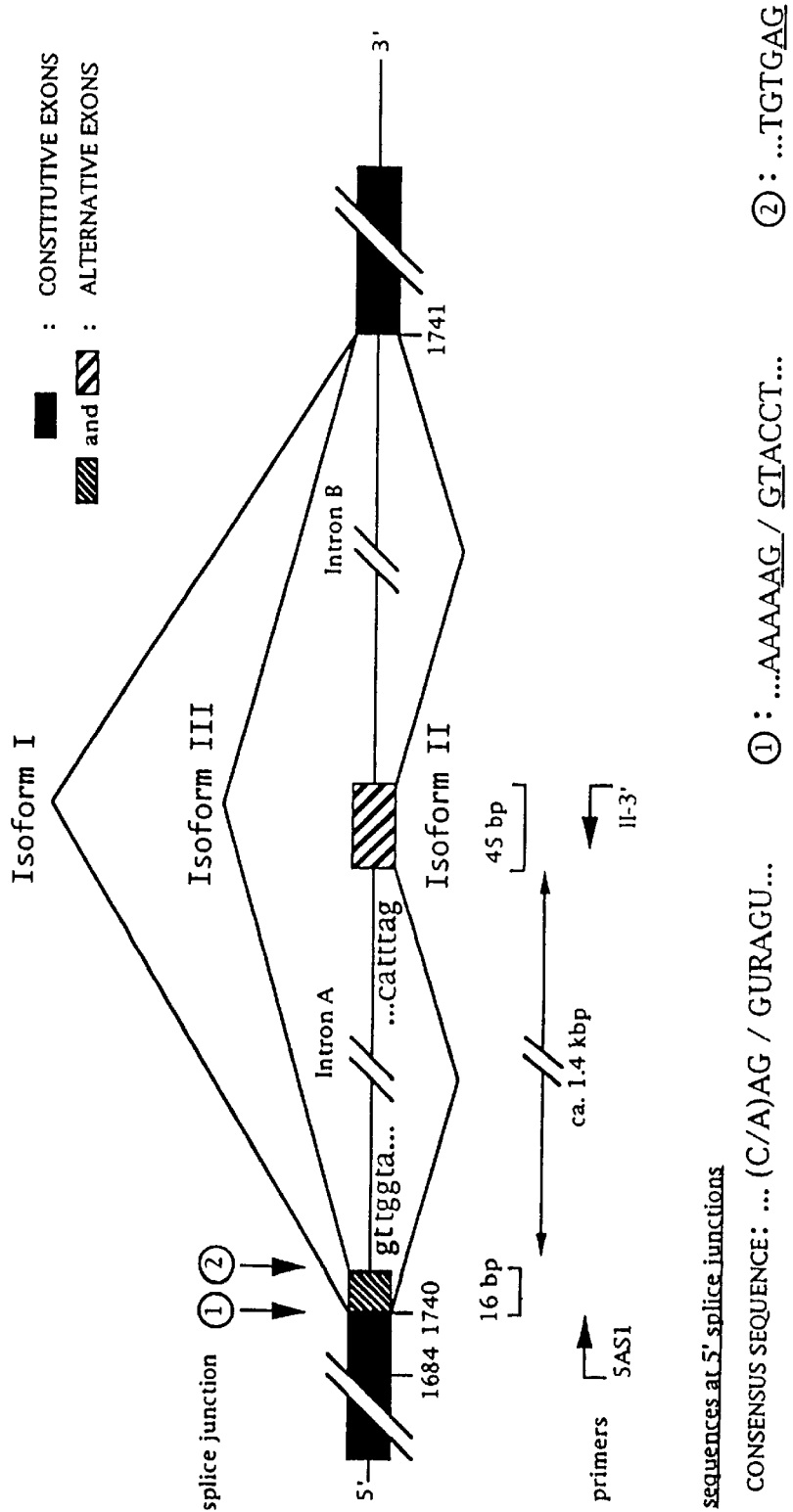
FIG. 5 depicts the mouse NF2 gene structure in the region of alternative splicing. Exons are represented by boxes, and flanking introns (A and B) by lines. Intronic sequences at the relevant splice junctions are indicated.

Two distinct modes of splicing appeared to be involved in the generation of isoforms I, II, and III. FIG. 5 shows a schematic description of the mouse NF2 gene structure in this region, as determined by sequence analysis of mouse genomic DNA. In genomic DNA, the 16 bp insertion sequence present in transcript isoform III is contiguous with and represents an extension of the upstream exon; no distinct intron separates the 5' constitutive exon from the alternative exon of 16 bp. In contrast, sequencing beyond the 16 nucleotides revealed an intronic sequence. Similarly, sequencing with primer II-3' revealed intronic sequences at the 5'-boundary of the 45 bp sequence found in isoform II cDNA. Thus, the 45 bp sequence represents a distinct exon and is separated from the 3' end of the 16 bp insertion sequence by about 1.4 kb. The different splicing pathways are shown by the diagonal lines.

The mechanisms of the different splicing pathways appear to include:

(a) alternative 5'-donor sites: transcript isoforms I and II are generated by usage of an alternative 5'-donor site within a particular exon, resulting in excision of an intron of different length and a reduction in exon size of 16 bp, as compared to that in isoform III.

(b) a casette exon: transcript isoform II is generated as a variant of isoform I by inclusion of a distinct alternative exon of 45 bp in length.

EXAMPLE IV

Detection of NF2 Transcript Isoforms in Different Mouse Tissues by RT-PCR Amplification The presence of NF2 transcript isoforms in different mouse tissues was detected by performing reverse transcriptase-PCR analysis of various mouse tissue RNAs using primers 5AS1 and 3AS1 flanking the alternative splice site at nucleotide 1740. The identify of all three PCR-amplified DNA fragments was confirmed by subcloning and sequencing. A variable pattern of expression was observed for the various transcript isoforms. Isoform II was more abundantly expressed than isoform I in tissues such as brain, heart, liver and lung. In contrast, isoform I was the predominantly expressed species in spleen and testis. Weak but detectable expression of isoform III was observed only in spleen and testis. Although originally identified as an isolated cDNA clone from a mouse brain cDNA library, no amplification of isoform III was detected in mouse brain.

EXAMPLE V

Detection of NF2 Transcript Isoforms in Different Mouse Tissues by Northern Blot Analysis In order to conduct a further analysis of the expression of NF2 in various mouse tissues, Northern blot analysis was performed. The mouse NF2 gene was found to be widely expressed in tissues such as heart, brain, spleen, lung, liver, skeletal muscle, kidney and testis. A single predominantly hybridizing species of about 6 kb was detected in all tissues, with highest expression in heart, brain and testis. These results indicate that the expression of the mouse NF2 gene is clearly not restricted to the central nervous system.

EXAMPLE VI

Detection of an NF2 Gene in Other Species

In order to determine whether the NF2 gene is conserved in species other than mouse, Southern blots were performed using a human NF2 cDNA probe. Filter-immobilized DNA (8 μg/lane) from differenct species was hybridized with a $^{32}$P-labeled human NF2 cDNA probe. Blots were exposed to Kodak X-AR films at −80° C. with intensifying screens from 2 hr to 3 days. Strong hybridization was detected to DNA from species such as rat, dog, cow, rabbit and chicken. These results indicate that the NF2 gene is highly conserved during evolution.

EXAMPLE VII

Expression of the NF2 Gene in Human Tissue

In order to evaluate the pattern of expression of the NF2 gene in humans, Northern blot analyses were performed using poly(A)$^+$ RNA isolated from various human tissues. Two major transcripts of approximately 2.6 kb and 7 kb, together with a weakly hybridizing species of 4.4 kb, were detected in heart, brain, lung, liver, skeletal muscle, kidney, pancreas, and placenta (a very faint signal was observed in overexposed Northern blots). PCR analysis also revealed the presence of NF2 gene transcripts in total RNA extracted from the eighth cranial nerve, adrenal gland and cerebellum, indicating that expression of the NF2 gene is not restricted to the CNS but occurs in a wide variety of human tissues.

EXAMPLE VIII

Alternative Splicing at the 3' End of the Human NF2 Gene Transcript

PCR analysis of the NF2 gene transcript using primers 5m6 and 3m6 revealed the presence of two distinct products of 350 bp and 395 bp in different human tissues including the eighth cranial nerve (the tissue from which vestibular schwannomas derive). Analysis of one of these transcripts confirmed a sequence identical to merlin, reported previously (Trofatter et al. (1993) *Cell* 72:791–800; Rouleau et al. (1993) *Nature* 363:515–521), whereas the product with higher molecular weight revealed a 45 bp insertion at nucleotide 1737, encoding eleven amino acids and a premature termination of the reading frame (FIGS. 6 and 7 (SEQ ID NO:9)). This insertion was also detected in an NF2 cDNA clone isolated from a fetal brain cDNA library. The novel isoform of the NF2 gene transcript, which presumably arises by alternative splicing, encodes a 590 amino acid protein with a modified C terminus. Therefore, the predicted C terminus of both NF2 gene products would differ by a total of sixteen amino acids. The novel NF2 gene alternative splice variant has been designated isoform II, and the original NF2 gene transcript published previously (Trofatter et al. (1993) *Cell* 72:791–800; Rouleau et al. (1993) *Nature* 363:515–521) as isoform I.

EXAMPLE IX

Identification of NF2 Isoforms in Different Human Tissues and Tumor Types

The location and predicted amino acid sequence of the alternative splice variant were found to be completely conserved in the mouse (see Example II). In addition, RNA PCR analysis showed marked differences in the relative abundances of both NF2 gene transcript isoforms in a number of tissues and tumor types. Whereas isoform II showed very low relative expression levels in adrenal gland and the eighth cranial nerve, isoform II of the NF2 gene transcript was the predominant species in RNA from cerebellum. By contrast, both isoforms showed similar expression levels in kidney. Similarly, differences in the relative expression levels of isoform I and II transcripts were observed in different tumor types. In particular, isoform II was expressed predominantly in three colon carcinomas analyzed with almost complete absence of isoform I.

RNA PCR analysis of one vestibular schwannoma (AN11) using oligonucleotide primers that flank the alternative splice site near the 3' end of the NF2 gene transcript (5m6 and 3m6) showed a unique fragment of reduced size (187-bp) in comparison with the products derived from isoforms I and II (350 bp and 395 bp, respectively) in normal tissue. Sequencing of the aberrant product confirmed a 163 bp deletion (nucleotides 1575–1737) that included the alternative splice site at nucleotide 1737 (Table 1). This deletion near the 3' end of the NF2 gene transcript would result in the removal of fifty four amino acids, including the C-terminal end of isoform II of merlin, and would introduce a frameshift in the reading frame of isoform I.

EXAMPLE X

NF2 Gene Mutations in Vestibular Schwannomas

To investigate the presence of mutations within the NF2 gene coding region in tumors typically associated with NF2, a PCR/SSCP analysis was performed in RNA from vestibular schwannomas.

A total of twelve sporadic and three NF2-associated vestibular schwannomas were screened (Table 1). A preliminary analysis of the PCR-amplified products by agarose gel electrophoresis revealed fragments of reduced size in five tumor samples, including tumors AN10 and AN825, wherein deletions in the NF2 gene transcript were evidenced by the presence of fragments of 269 bp and 251 bp, respectively. SSCP analysis of the remaining cases detected a variant electrophoretic pattern in three additional tumors, including AN13. Cloning and double strand sequencing of the aberrant RNA PCR fragments demonstrated the presence of mutations in each of the tumors showing products of altered size. As summarized in Table 1, mutations within the NF2 coding region were detected in two of three hereditary and in six of twelve sporadic vestibular schwannomas. One tumor (AN11) carried a NF2 cDNA deletion that introduced a frameshift resulting in premature termination of the reading frame within 56 bp of the deletion breakpoint (Table 1). The remaining seven vestibular schwannomas exhibited in-frame transcript deletions that would result in truncated proteins without altering the distal reading frame (Table 1). In some tumors (AN94, AN10, AN54, AN72 and AN825), in-frame cDNA deletions represented whole exons. The total absence of RNA PCR products derived from the normal allele was observed in five vestibular schwannomas (Table 1, tumors AN94, AN11, AN13, AN825, and AN72), consistent with the highly homogeneous nature of this tumor type which only exhibits minor contamination of non-neoplastic tissue.

The origin of the mutations was confirmed by screening lymphocyte genomic DNA from the patients. Mutation analysis of blood DNA from the patients bearing sporadic vestibular schwannomas AN94, AN10, AN11, AN54, AN72 and AN825 did not reveal any alterations in the NF2 gene, including the exon/intron junctions flanking the sequences deleted in the tumor cDNAs, thus confirming the somatic nature of these mutations (Table 1).

EXAMPLE XI

Analysis of Tumor Types Seemingly Unrelated to NF2

Since losses affecting chromosome 22q have been reported to occur in a variety of neoplasms, somatic mutations in the NF2 gene might be implicated not only in tumors typically associated with NF2 but also in seemingly unrelated cancers. Therefore, different tumor types from non-NF2 individuals, including breast and colon carcinomas, malignant melanomas, and pheochromocytomas, were screened for mutations within the NF2 gene coding region. Because NF2 is predominantly associated with tumors derived from the embryonic neural crest, a series of sporadic pheochromocytomas and melanomas, two tumor types that do not show a higher incidence in NF2 patients, were analyzed. Of three primary melanomas and seventeen melanoma metastases analyzed, sequencing of aberrant SSCP conformers demonstrated the presence of NF2 gene transcript mutations in six tumors. As shown in Table 1, in-frame deletions were detected in one primary skin melanoma (tumor 94771; superficial spreading type) and one melanoma metastasis (tumor 87506). The latter also exhibited an A to T transversion resulting in a nonconservative substitution of lysine to isoleucine (Table 1). The mutations detected in the remaining four melanoma metastases consisted of deletions of 1–143 bp that altered the reading frame generating premature stop codons (Table 1). A restriction enzyme map of the NF2 gene transcript indicated that the deletion observed in tumor 95540 would result in loss of a Bgl II site. Southern blot analysis of tumor DNA digested with Bgl II revealed an aberrant restriction pattern as compared to the control DNA, suggesting that the cDNA deletion described above is present at the genomic level. No apparent mutations in the NF2 cDNA were detected in five sporadic pheochromocytomas screened by RNA PCR/SSCP analysis.

Of fourteen primary breast carcinomas analyzed by RNA PCR/SSCP methods, one tumor showed a fragment of altered mobility. Sequence analysis of the altered-size PCR product demonstrated that this tumor, diagnosed as a poorly differentiated breast ductal carcinoma, carried a deletion of 211 bp that resulted in a frameshift, thereby introducing a premature termination codon within 74 bases of the deletion breakpoint (Table 1). Sequencing of this product also showed an A to T transversion at nucleotide 817 that would result in a substitution of isoleucine by phenylalanine (Table 1). This mutation was not detected in DNA from normal surrounding tissue, thus ruling out the possibility of a polymorphism. No apparent mutations in the NF2 gene coding region were detected in RNA samples extracted from twenty colon carcinomas.

EXAMPLE XII

Location of the NF2 Gene Transcript Deletions

Figure 8:
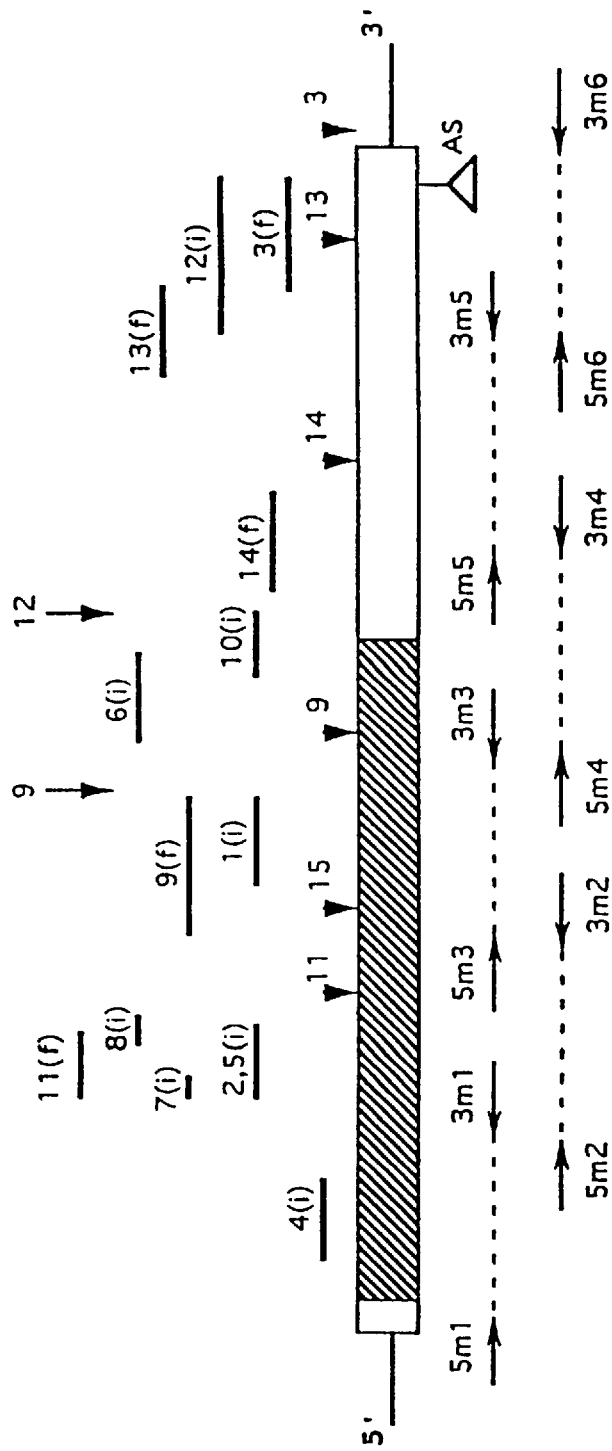
FIG. 8 is a schematic drawing showing the relative position of NF2 gene transcript mutations in different human tumor types. Numbers represent the tumors listed in Table 1 (1–15). Solid lines represent inframe (i) or frameshift (f) deletions. Vertical arrows indicate point mutations. The vertical arrow for sample No. 15 (melanoma 90021) represents a 1 bp deletion. The location of stop codons generated by frameshifts in the reading frame is indicated by solid vertical triangles. The coding region homologous to moesin, ezrin and radixin is represented by a hatched box. AS, alternative splice site. PCR oligonucleotide primers are represented by horizontal arrows.

An initial understanding of the potential functional significance of the different domains of the merlin protein may be gained from the location of the NF2 gene transcript deletions and their predicted effects on protein structure. Most of the alterations detected in this study (15 of 17 mutations; FIG. 8) are predicted to generate truncated proteins as the result of in-frame deletions or premature stop codons generated by reading frameshifts or point mutations. In most cases, these truncations would result in the removal of distal domains, including the α-helical and C-terminal regions, from the merlin protein. Although in some tumors the reading frame is preserved distal to the deletion breakpoint, it is likely that these dramatic alterations, which in some cases comprise whole exons, disrupt domains critical for merlin protein function. Evidence for function of the C terminus of merlin is provided by the frameshift deletion detected in vestibular schwannoma AN11 (Table 1), representing the most distal alteration. In this regard, the homozygous nature of this mutation, that predicts the removal of fifty four C-terminal amino acids, suggests that this region might be of critical importance for the putative tumor suppressor function of merlin.

TABLE 1

NF2 gene transcript mutations in human tumours.

| Tumour* | Histopathology** | Mutation† | Position†† | Effect¶ |
|---|---|---|---|---|
| 1) AN94 (s) | VS (S) | D135-bp | 676–810 | D (i) |
| 2) AN10 (s) | VS (S) | D84-bp | 364–447 | D (i) |
| 3) AN11 (s) stop(1793) | VS (S) | D163-bp | 1575–1737 | (f) > |
| 4) AN54 (s) | VS (S) | D126-bp | 115–240(113–238) | D (i) |
| 5) AN72 (s) | VS (S) | D84-bp | 364–447 | D (i) |
| 6) AN825 (s) | VS (S) | D114-bp | 886–999(888–1001) | D (i) |
| 7) AN13 (h) | VS (N/A) | D18-bp | 358–375 | D (i) |
| 8) AN26 (h) | VS (N/A) | D57-bp | 433–489 | D (i) |
| 9) 86336 | breast ductal CA | D211-bp | 600–810 | (f) > stop(884) |
|  |  | A > T | 817 | $Ile^{273}$ > Phe |
| 10) 94771 | melanoma | D87-bp | 1000–1086 (1003–1089) | D (i) |
| 11) 95540 | melanoma (m) | D85-bp | 361–445 | (f) > stop(518) |
| 12) 87506 | melanoma (m) | D228-bp | 1504–1731 (1501–1728) | D (i) |
|  |  | A > T | 1091 | $Lys^{364}$ > Ile |
| 13) 95783 | melanoma (m) | D125-bp | 1447–1571 | (f) > stop(1646) |
| 14) 86-20 | melanoma (m) | D143-bp | 1123–1265 | (f) > stop(1323) |
| 15) 90021 | melanoma (m) | D1-bp | 616 | (f) > stop(623) |

*(s) sporadic and (h) hereditary tumour.
**VS, vestibular schwannoma; (S), somatic origin of the mutation; (N/A), no blood from the patient was available; CA, carcinoma; (m), metastasis.
†D, deletion. The number of base pairs deleted follows the corresponding symbol.
††Nucleotide position of the mutations relative to the NF2 gene initiation codon. Alternative nucleotide positions (due to the repeated nature of the deleted sequence boundaries) are given in parenthesis.
¶D, deletion; (i), in-frame; (f), frameshift. The number in parenthesis indicates the nucleotide position of the stop codon generated by the frameshift.

Thus, novel NF2 transcript isoforms and NF2-encoded proteins, as well as antibodies generated thereto, have been disclosed. Although preferred embodiments of the subject invention have been described in some detail, it is to be understood that obvious variations can be made without departing from the spirit and the scope of the invention as defined by the appended claims.

What is claimed is:

1. An isolated protein encoded by mouse NF2 transcript isoform I, wherein said protein comprises the mouse amino acid sequence depicted in FIGS. 1A–1B (SEQ ID NO:2).

2. An isolated protein encoded by mouse NF2 transcript isoform II, wherein said protein comprises the amino acid sequence depicted in FIG. 2 (SEQ ID NO:5).

3. An isolated protein encoded by mouse NF2 transcript isoform III, wherein said protein comprises the amino acid sequence depicted in FIG. 3 (SEQ ID NO:7).

4. An isolated protein encoded by human NF2 transcript isoform II, wherein said protein comprises the amino acid sequence depicted in FIGS. 7A–7D (SEQ ID NO:10).

* * * * *